United States Patent
Wurm et al.

(10) Patent No.: US 11,746,360 B2
(45) Date of Patent: Sep. 5, 2023

(54) EUKARYOTIC CELL TRANSFECTION SYSTEMS AND RELATED METHODS

(71) Applicants: Florian M. Wurm, Montreux (CH); Maria J. Wurm, Montreux (CH); Maria de Lourdes Rodrigues, Collombey (CH); Divor Kiseljak, Renens (CH); Cedric Bürki, Pully (CH); Cyril Pugin, Vevey (CH); Guillaume Raussin, Aigle (CH); Julie Heymoz, Lausanne (CH)

(72) Inventors: Florian M. Wurm, Montreux (CH); Maria J. Wurm, Montreux (CH); Maria de Lourdes Rodrigues, Collombey (CH); Divor Kiseljak, Renens (CH); Cedric Bürki, Pully (CH); Cyril Pugin, Vevey (CH); Guillaume Raussin, Aigle (CH); Julie Heymoz, Lausanne (CH)

( * ) Notice: Subject to any disclaimer, the term of this patent is extended or adjusted under 35 U.S.C. 154(b) by 424 days.

(21) Appl. No.: 16/788,303

(22) Filed: Feb. 11, 2020

(65) Prior Publication Data
US 2020/0263203 A1    Aug. 20, 2020

Related U.S. Application Data

(60) Provisional application No. 62/803,639, filed on Feb. 11, 2019.

(51) Int. Cl.
*C12N 15/87* (2006.01)
*C12N 5/07* (2010.01)
*C12N 5/071* (2010.01)

(52) U.S. Cl.
CPC ........... *C12N 15/87* (2013.01); *C12N 5/0601* (2013.01); *C12N 5/0602* (2013.01); *C12N 2500/50* (2013.01); *C12N 2510/04* (2013.01)

(58) Field of Classification Search
CPC .................................................. C12N 15/87
See application file for complete search history.

(56) References Cited

FOREIGN PATENT DOCUMENTS

| WO | 2016/178233 | 11/2016 |
| WO | 2017/011598 | 1/2017 |

OTHER PUBLICATIONS

Longo, 2013, methods Enzymol, 529:227-240.*
Biocompare, https://www.biocompare.com/20024-MEM-w-Lglutamine-Powder/68084-GIBCO-OptiMEM-I-ReducedSerum-Medium-powder/, accessed on Feb. 17, 2022; printout attached.*
Hacker DL, Kiseljak D, Rajendra Y, Thurnheer S, Baldi L, Wurm FM. Polyethyleneimine-based transient gene expression processes for suspension-adapted HEK-293E and CHO-DG44 cells. Protein Expr Purif. Nov. 2013;92(1):67-76. doi: 10.1016/j.pep.2013.09.001. Epub Sep. 8, 2013. PMID: 24021764; PMCID: PMC7129890.
Shen X, Pitol AK, Bachmann V, Hacker DL, Baldi L, Wurm FM. A simple plasmid-based transient gene expression method using High Five cells. J Biotechnol. Dec. 20, 2015;216:67-75. doi: 10.1016/j.jbiotec.2015.10.007. Epub Oct. 23, 2015. PMID: 26476358.
Kadlecova Z, Nallet S, Hacker DL, Baldi L, Klok HA, Wurm FM. Poly(ethyleneimine)-mediated large-scale transient gene expression: influence of molecular weight, polydispersity and N-propionyl groups. Macromol Biosci. May 2012;12(5):628-36. doi: 10.1002/mabi.201100404. Epub Mar. 13, 2012. PMID: 22411776.

* cited by examiner

*Primary Examiner* — Valarie E Bertoglio
(74) *Attorney, Agent, or Firm* — JWIP & Patent Services, LLC; Jacob G. Weintraub, Esq.

(57) ABSTRACT

The present invention provides robust, streamlined, reproducible and highly efficient eukaryotic cell transfection systems and related methods. The highly-efficient systems and methods of the present invention reduce the number of steps required to transfect cells and reduce, e.g., eliminate, the need for specialized equipment. In particular, the systems and related methods afford the ability for streamlining transfection while retaining and improving robust and reproducible transfection efficiencies, cell viability, and/or protein production. Furthermore, the highly-efficient systems and methods of the present invention for transfecting eukaryotic cells also eliminate the need for any specialized or complicated preparation of exogenous nucleic acid, which makes available high throughput and/or large scale transfection.

18 Claims, 14 Drawing Sheets

EUKARYOTIC CELL TRANSFECTION SYSTEMS AND RELATED METHODS

RELATED APPLICATIONS

This application claims priority to U.S. Provisional Patent Application No. 62/803,639, filed on Feb. 11, 2019; the entirety of which is incorporated herein by reference.

BACKGROUND OF THE INVENTION

Many of today's biologic drug therapies (biologicals) are produced using genetically transformed (transgenic or recombinant) eukaryotic cells, for example, using recombinant mammalian cells. In fact, in terms of specialized reagents and equipment, the market for the generation of transgenic or recombinant eukaryotic cells is expected to exceed one billion dollars in sales by 2022. Biologicals of interest in this context are recombinant proteins, such as antibodies, enzymes, fusion molecules and the like, as well as more complex products such as virus-like particles, retrovirus like vectors, and any other protein, DNA or RNA.

The putative process of generating transformed cells to express a gene of interest. e.g., recombinant eukaryotic cells, is a multi-step, multi-day series of processes, beginning with proper design of the nucleic acid construct to be used and choice of an appropriate cell line. Subsequent steps involve the growth of the selected cells in culture and introduction of the nucleic acid through the cellular membrane into the cells. This process is typically called transfection. Following successful transfection, the cells are grown under conditions to express the gene or genes encoded by the nucleic acid, and the gene products, e.g., protein products, are then harvested for use.

Despite the passage of over fifty years since the first successful mammalian cell transfection, the introduction of nucleic acid into eukaryotic cells, such as mammalian cells, has remained a complex and highly error-prone procedure that rarely provides predictable results. Numerous chemical, physical, and viral methods requiring specific reagents and equipment have been employed. The disadvantages of these methods are numerous and well known to the skilled artisan, including being labor and time intensive, as well as requiring: specialized equipment and techniques, cumbersome preparation of nucleic acids, reagents and cells, long and difficult-to-control pre-culture of cells, damage to the recipient cells, e.g., cell toxicity, damage to the nucleic acid, poor transfection efficiencies, poor gene expression rates, and poor product recovery. There has also been a need for repeated and tedious preparation of fresh reagents for transfections which are done over different time frames reduces the reproducibility of experiments, since several reactions between nucleic acids and the corresponding transfection reagents are poorly understood and can be influenced by numerous physical and chemical parameters.

Such complex preparation methods are also prohibitive to the ability to carry out either high-throughput testing of large numbers of nucleic acid constructs in one or more eukaryotic cell cultures or to execute transfection of and subsequent product recovery from cells at a large scale for the production of large quantities of product. Thus, there is a need in the art for a streamlined, robust, error-reducing, more predictable and/or a highly-efficient approach to transfecting cultivated eukaryotic cells (such as mammalian, insect or fish cells) with a desired nucleic acid.

SUMMARY OF THE INVENTION

Accordingly, the present invention provides robust, streamlined, error-reducing and highly efficient eukaryotic cell transfection systems and related methods. The highly-efficient systems and methods of the present invention reduce the number of steps required to transfect cells and reduce, e.g., eliminate, the need for specialized equipment. In particular, the systems and related methods afford the ability for streamlining transfection while retaining robust transfection efficiencies, and increase cell viability, cell number and/or protein production and overall reproducibility. Furthermore, the highly-efficient systems and methods of the present invention for transfecting eukaryotic cells makes transfection available for both high throughput approaches and/or for large scale transfection.

As such, one aspect of the invention provides a highly-efficient eukaryotic cell transfection (HECT) system that is capable of mediating transfection of purified, unencumbered exogenous nucleic acid into a eukaryotic cell comprising a cell transfection medium pre-conditioned with a positively charged polymer, e.g., polyethylenimine.

Another aspect of the present invention provides a highly-efficient eukaryotic cell transfection (HECT) method. The method comprises the steps of obtaining a cell transfection medium pre-conditioned with a positively charged polymer that is capable of mediating transfection of purified, unencumbered exogenous nucleic acid into eukaryotic cells; combining eukaryotic cells with said pre-conditioned cell transfection medium to produce cell-supplemented pre-conditioned cell transfection medium; and combining said cell-supplemented pre-conditioned cell transfection medium with purified, unencumbered exogenous nucleic acid, such that said purified, unencumbered exogenous nucleic acid is transfected into said eukaryotic cells in a highly-efficient manner.

In another aspect, the present invention provides a kit for high-efficiency transfection of eukaryotic cells comprising a pre-conditioned eukaryotic cell transfection medium of the present invention; eukaryotic cells compatible with said pre-conditioned transfection medium, wherein said eukaryotic cells are selected from the group consisting of mammalian cells, insect cells, fish cells and avian cells; and a DNA vector compatible with said eukaryotic cells.

BRIEF DESCRIPTION OF THE FIGURES

Advantages of the present invention will be apparent from the following detailed description, which description should be considered in combination with the accompanying figures, which are not intended to limit the scope of the invention in any way.

DETAILED DESCRIPTION OF THE INVENTION

Figure 1:
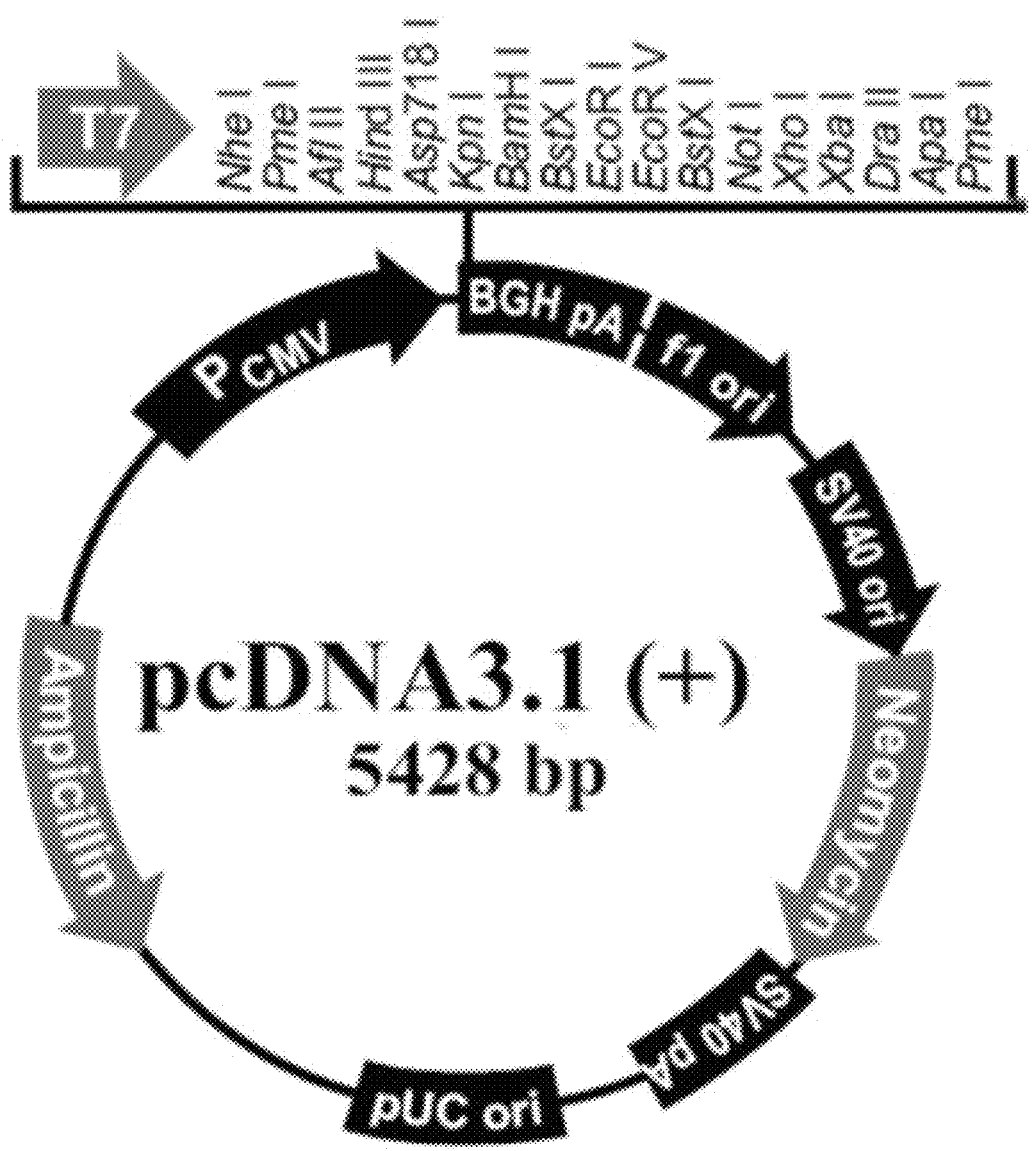
FIG. 1 is a plasmid map of the commercially available pcDNA™3.1 (Invitrogen) for use in certain embodiments of the present invention. Modified versions of this plasmid are capable of supporting the expression of proteins in mammalian cells.
Figure 2:
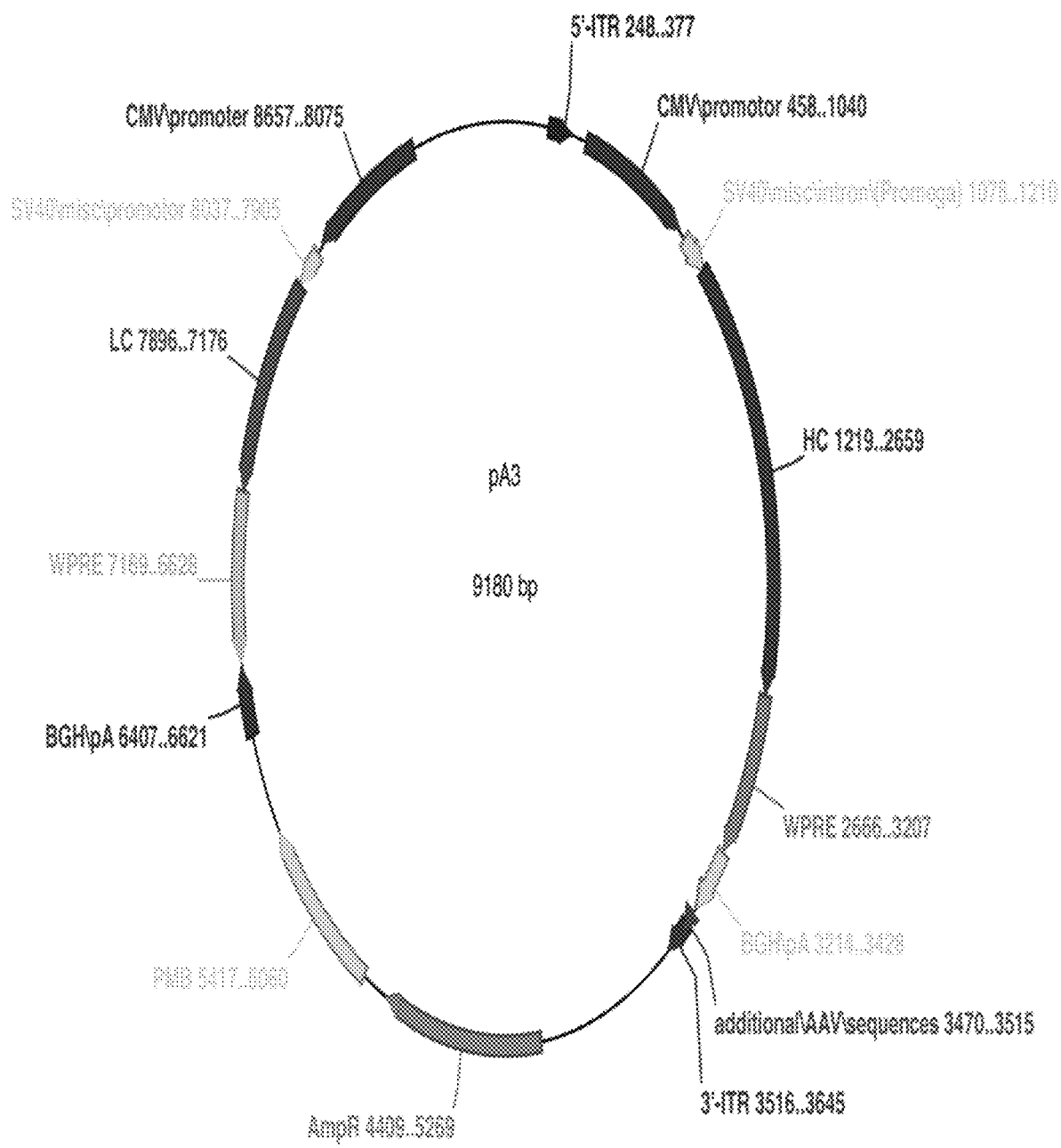
FIG. 2 is a plasmid map of the ExcellGene vector pA3 for use in certain embodiments of the present invention. It is capable of supporting the expression of an Immunoglobulin (IgG) in mammalian cells.

Despite existing efforts in the advancement of protein production, these known/existing efforts have yet to yield any significant improvements to transfection efficiencies, transfection reproducibility, transfection result predictability, cell viability, protein production, or quality of protein produced in cell cultures ranging from very small volumes (e.g., $\Xi l$ or $\eta l$ quantities) to the large volumes of bioreactors. In contrast, the highly-efficient eukaryotic cell transfection (HECT) systems, media, and methods of the present invention provide robust, streamlined, reproducible, predictable, user-friendly systems and methods resulting in high transfection efficiencies, high cell viability, and protein yield.

The highly-efficient systems, media, and methods of the present invention reduce the number of steps required to transfect cells and reduce, e.g., eliminate, the need for specialized equipment. In particular, the systems, media, and related methods afford the ability for streamlining transfection while retaining robust, efficient, and reproducible transfection efficiencies, cell viability, and/or protein production. Furthermore, the highly-efficient systems, media, and methods of the present invention for transfecting eukaryotic cells also reduce, e.g., eliminate, the need for any specialized or complicated preparation of exogenous nucleic acid, which makes transfection available and reproducible for both high throughput approaches and for large scale transfection.

The present invention, including systems, media, and methods will be described with reference to the following definitions that, for convenience, are set forth below. Unless otherwise specified, the below terms used herein are defined as follows:

1. Definitions

As used herein, the terms "a," "an," "the" and similar terms used in the context of the present invention (especially in the context of the claims) are to be construed to cover both the singular and plural unless otherwise indicated herein or clearly contradicted by the context.

The term "about" is used herein in reference to the degree or extent of the term which it modifies, and that such extent may be 100% or near to but not exactly 100% of the modified term; industry accepted standards will assist in defining the quantitative aspects of how "near" 100% is defined. In particular embodiments, the term "about" indicates ±2%, ±1% or ±0.5%. In a particular embodiment, for example, the language "about 19%" would be exactly 19%; and in an alternative particular embodiment, for example, the language "about 19%" would mean 19%±2%, 19%±1%, or 19%±0.5%.

The term "eukaryotic" is well understood in the art and used herein to describe cells that contain a nucleus, e.g., eukaryotic cells. Eukaryotic cells include, but are not limited to, mammalian cells, e.g., human cells or animal cells, insect cells, fish cells, plant cells, fungal cells, and avian cells.

The term "exogenous nucleic acid" is used herein to describe that nucleic acid (e.g., DNA or RNA) which is introduced into a cell (e.g., a eukaryotic cell or a prokaryotic cell). The exogenous nucleic acid may have a nucleotide sequence that is 0% to 100% identical to, or complementary to, a DNA or RNA sequence already existing in the recipient cell.

The term "highly-efficient" is used herein to describe the advantages of the eukaryotic cell transfection system and methods of the present invention, which include one or more of the following advantages: (1) an increase in the percentage of cells successfully transfected as compared with existing methodologies/systems, e.g., 30% or greater of cells transfected, e.g., 50% or greater of cells transfected, e.g., 75% or greater of cells transfected, or e.g., 99% or greater of cells transfected; (2) an increase in the amount of product recovered from successfully transfected cells as compared with existing methodologies/systems, e.g., at least a 2-fold increase, e.g., at least a 5-fold increase, e.g., at least a 10-fold increase, e.g., at least a 20-fold increase, e.g., at least a 50-fold increase in product recovery, e.g., at least a 100-fold increase, or e.g., at least a 500-fold increase; (3) increased cell viability post-transfection as compared with existing methodologies/systems, e.g., 50% or greater cell viability, e.g., 60% or greater cell viability, e.g., 70% or greater cell viability, e.g., 80% or greater cell viability, e.g.,90% or greater cell viability, or e.g.,99% or greater cell viability; (4) an increase in cell number (in cells/ml) after transfection during the production phase as compared with existing methodologies/systems, e.g., a 10% or greater number of cells, e.g., a 20% or greater number of cells, e.g., a 30% or greater number of cells, e.g., a 50% or greater number of cells, e.g., a 75% or greater number of cells, e.g., a 100% or greater number of cells, e.g., a 150% or greater number of cells, e.g., a 300% or greater number of cells, e.g., a 500% or greater number of cells; (5) a higher reproducibility of transfections within an experiment as compared with existing methodologies/systems, for example, intra-experimental reproducibility (i.e., when multiple transfection are executed with the same seed cell culture), or for example, inter-experimental reproducibility (i.e., when done with seed cell cultures from different sources or when done on different days); and (6) elimination of laborious nucleic acid protection procedures as compared with existing methodologies/systems including, but not limited to, encapsulation or association of nucleic acid with or in liposomes, dendrimers, cyclodextrins, or cationic polymers, e.g., DEAE-dextran, e.g., polyethylenimine, e.g., polylysine and the like, nano-particles, metals, formation of calcium phosphate-DNA complexes, use of viral carrier vectors, and the like.

The term "mammalian cell" is also well understood in the art and is used herein to describe any primary cell, primary cell culture, or cultured cell line derived from a mammal. The term "animal cell" is also well understood in the art and is used herein to describe any primary cell or cultivated cell derived from a mammalian or non-mammalian species, such as fish, reptile or bird species, including cells from non-vertebrate species such as metazoans e.g., eukaryotic species with more than one cell).

The term "nucleic acid" is known in the art and used herein to described natural or synthetic polymers of deoxyribonucleic acid (DNA) (e.g., single-stranded or double-stranded), or ribonucleic acid (RNA), or polymers comprising a mix of both deoxyribonucleotides and ribonucleotides (DNA-RNA hybrids), peptide nucleic acid (PNA), or locked nucleic acid (LNA), and the like. As used herein, the term encompasses all forms and types of DNA, RNA, DNA-RNA hybrids, PNA or LNA contemplated for transfection into eukaryotic cells.

The term "polyethylenimine" (PEI) is known in the art and used herein to describe a polymer of repeating units composed of an amine group and two carbon aliphatic spacers, e.g., $(C_2H_5N)_n$. Due to the polymeric nature of PEI, polymers may range in molecular weight from about 800 Da to about 25 KDa to 1000 KDa or more.

PEI polymers may be acylated or deacylated. Polymers of PEI may be linear, for example,

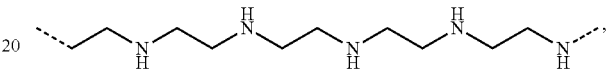

or branched, for example,

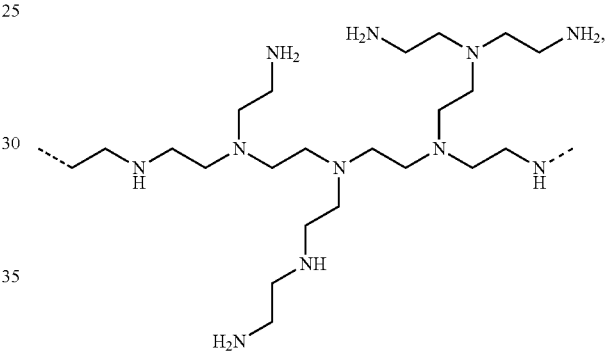

where the dashed lines represent the locations where the monomeric unit connects to another monomeric unit in the polymeric chain. These polymers can also be hyperbranched and/or dendritic. In certain embodiments, a given amount of a PEI polymer, e.g., a PEI polymer of 25 KDa, is polydisperse, i.e., comprises a range of molecules of different molecular weights having an average molecular weight of 25 KDa. In certain embodiments, identification of a molecular weight of a PEI polymer in this disclosure of the invention is to be understood to be of polydispersed character where the synthesis of PEI polymer is not uniform and may have produced a distribution of polymers with an "averaged" molecular weight.

The term "pre-conditioned" is used herein to describe the characteristic of a combination of two or more components which have been treated, conditioned or exposed to another agent or component (e.g., a pre-conditioning agent), prior to the introduction of one or more additional items (e.g., a nucleic acid, a compound, a solution, or a cell). For example, in certain embodiments, the cell transfection media of the invention are "pre-conditioned", that is pre-mixed with or pre-exposed to polyethylenimine prior to exposure of the media to another compound or solution, e.g., to eukaryotic cells targeted for transfection, or e.g., to purified, unencumbered exogenous nucleic acid.

The language "purified, unencumbered" is used herein to describe the form and condition of exogenous nucleic acid having the characteristic of being free from compounds, molecules, chemicals, and treatments usually employed in eukaryotic cell transfections, and which may be required to facilitate transfection in traditional methodology. For example, the purified, unencumbered nucleic acid utilized in the systems and methods of the present invention are free of (e.g., essentially free of), liposomes, dendrimers, cyclodextrins, or cationic polymers, e.g., DEAE-dextran, polylysine, polyethylenimine and the like, nano-particles, metals, formation of calcium phosphate-DNA complexes, use of viral carrier vectors, viral protein capsules, and the like. Purified, unencumbered exogenous nucleic acids may exist in an essentially solvent-free form, e.g., as a pure, precipitated pellet of material, or dissolved in an aqueous solution such as purified water, or TE buffer, e.g., 10 mM Tris 1 mM EDTA buffer, and the like.

The term "recipient cell" is used herein to describe a cell, e.g., a mammalian cell (e.g., a CHO cell), that is subjected to a transfection process, e.g., the highly-efficient method of nucleic acid introduction into eukaryotic cells of the invention, and is the first and direct recipient of the exogenous nucleic acid, e.g., exogenous DNA.

The term "species" is used herein to describe related variants of a particular cell type. For example, the first Chinese hamster ovary cells were isolated and immortalized in the late 1950's; since that time numerous variations or species of the original CHO cells, CHO-ori, have arisen, such as CHO-K1, CHO-S, CHO-DXB11, CHO-DG 44 and others. As used herein, CHO encompasses all species of CHO cells referred to in the art as a type of CHO cell, e.g., CHO-K1, CHO-S, CHO-DXB11, CHOExpress™, and CHO-DG 44 are all examples of species of CHO cells.

The term "transfection" is known in the art and used herein to describe the deliberate introduction of nucleic acids, e.g., exogenous nucleic acids, e.g., exogenous DNA, into eukaryotic cells. Eukaryotic cells may be transiently transfected or stably transfected. Transiently transfected eukaryotic cells take up and express exogenous nucleic acids, e.g., exogenous DNA, where the nucleic acid e.g., exogenous DNA, is generally not incorporated into the genome of the transfected cell. In contrast, for stable transfections, the exogenous nucleic acid, e.g., exogenous DNA, is incorporated into, e.g., integrated into, the genome of a stably transfected recipient cell; the exogenous nucleic acid, e.g., exogenous DNA, is replicated each time the genome is replicated prior to nuclear and/or cell division, and is passed through to multiple generation of cells, e.g., daughter cells. Stably transfected, eukaryotic cells may also be referred to as recombinant cells.

II. Highly-Efficient Eukaryotic Cell Transfection (HECT) Systems of the Invention One embodiment of the present invention provides a highly-efficient eukaryotic cell transfection (HECT) system that is capable of mediating transfection of purified, unencumbered exogenous nucleic acid into a eukaryotic cell comprising a cell transfection medium pre-conditioned with a positively charged polymer, e.g., polyethylenimine. The systems of the present invention have the capability to mediate transfection of purified, unencumbered exogenous nucleic acid into a eukaryotic cell; however, this does not require actual mediation to have such potential or ability to mediate.

A particular advantage of the HECT systems and methods of the invention is the ability of transfection media pre-conditioned with a positively charged polymer, e.g., polyethylenimine,(e.g., 10 KDa PEI, or e.g., 25 KDa PEI, or e.g., 40 KDa PEI), to result in the transfection of eukaryotic cells with purified, unencumbered exogenous nucleic acid, e.g., naked DNA, or e.g., naked RNA, without the requirement of any other experimental step. Given that eukaryotic cell membranes and nucleic acids are both negatively charged, requiring modification of either (or both) the cell membrane or the nucleic acid to permit transfer of the extra-cellular exogenous nucleic acid across the cell membrane and into the cell, traditional methods that have been previously employed to alter the cell membrane often rely upon force, mechanical or electric, chemicals, or infectious agents, each of which carries a high risk of damage to the cell and, in some cases, to the nucleic acid.

Solutions of PEI have been known to have be cumbersome to make, take almost an entire day for preparation (see for example, Example 1C) and are very viscous in nature. In fact, it has been difficult in existing methods to thoroughly and homogeneously make PEI solutions and to efficiently mix them with solutions of nucleic acids. The very mechanics of mixing the nucleic acid molecules with the viscous PEI solution is known to have resulted in shearing or other damage to the nucleic acid. In addition, the ratio of nucleic acid to PEI resulting in the best transfection efficiency may be determined for each PEI and nucleic acid preparation and must take into consideration the cell type and its' corresponding medium.

Furthermore, the amount of time the nucleic acid solution is exposed to the PEI solution may affect transfection and may also need to be optimized. What is more is PEI has been shown to be toxic to eukaryotic cells, particularly affecting various intracellular processes, and often resulting in death of the cell. Thus, transfection of eukaryotic cells using nucleic acid:PEI complexes require considerable effort; from preparing a homogeneous mixture with the desired nucleic acid, to the determination of the correct ratio of PEI to nucleic acid to allow for adequate cell transfection with the least amount of cell toxicity.

In this way, the two major difficulties that have previously arisen when PEI has been used in the traditional manner to transfect eukaryotic cells, i.e., viscosity and toxicity, have been overcome by the solutions provided in the systems and the methods of the present invention. The simplified HECT systems and methods of the present invention address the issues of viscosity and toxicity, eliminating the need to mix exogenous nucleic acid with PEI, (thus also eliminating the need to determine an optimum exposure time for the nucleic acid with the PEI), reducing cell toxicity, and increasing cell viability and cell growth post transfection, transfection efficiency, and expression of desired products, e.g., proteins, or e.g., viral particles. Other advantages offered by the eukaryotic cell transfection system, method and pre-conditioned media of the invention include a decrease in the amount of time and materials required for transfection of eukaryotic cells, e.g., mammalian cells, such as a reduction in the number of steps, e.g., a reduction in the amount of "hands-on" experimental time required, compared to standard and customary methods in the art, and reducing the need for specialized transfection equipment. A further advantage of the eukaryotic cell transfection system, method and pre-conditioned media of the invention include the ability of the pre-conditioned media to support and facilitate cell growth as well as cell transfection, reducing the need for multiple types of media, specialized reagents, media changes, "hands on" experimental time, and disruption to the cells. Finally, due to the ability to store an optimized pre-conditioned cell transfection medium in aliquots for extended periods of time without the loss of activity and efficiency, transfections in experiments that are done repeatedly either simultaneously or spread over extended periods of time have a higher reproducibility. Such approaches can also distinguish the effects of different culture conditions prior to transfection, since the only variant in an experiment are the cells derived from such variant pre-cultures, whereas the pre-conditioned cell transfection medium remains the same from experiment to experiment.

In certain embodiments of the invention, the highly-efficient eukaryotic cell transfection (HECT) system is low-temperature-stable, wherein the media, e.g., pre-conditioned media, is further capable of being held at 4° C., e.g., at least 30 days, and retaining the ability to mediate transfection of at least 10% of recipient eukaryotic cells with purified, unencumbered exogenous nucleic acid. In certain embodiments, the low-temperature-stable media, e.g., pre-conditioned media, retains the ability to support and promote cell growth. In certain embodiments, the positively charged polymer is polyethylenimine, wherein the polyethylenimine is 25 KDa in molecular weight. In certain embodiments, the positively charged polymer is polyethylenimine, wherein the polyethylenimine is 10 KDa in molecular weight. In certain embodiments, the positively charged polymer is polyethylenimine, wherein the polyethylenimine is 40 KDa in molecular weight. In certain other embodiments, the positively charged polymer is a mixture of polyethylenimines of different average molecular weights, e.g., having average molecular weights ranging from 1 KDa to 50 KDa, e.g., 10 KDa to 40 KDa, or e.g., a mixture of 10 KDa and 25 KDa PEI.

In certain embodiments of the invention, the highly-efficient eukaryotic cell transfection (HECT) system is freeze-stable, wherein the media, e.g., pre-conditioned media, is further capable of being frozen, e.g., at least 30 days or 60 days, or 90 days and retaining the ability to mediate transfection of at least 10% of recipient eukaryotic cells with purified, unencumbered exogenous nucleic acid. In certain embodiments, the freeze-stable media, e.g., pre-conditioned media, retains the ability to support and promote cell growth. In certain embodiments, the positively charged polymer is polyethylenimine, wherein the polyethylenimine is 10 KDa in molecular weight. In certain embodiments, the positively charged polymer is polyethylenimine, wherein the polyethylenimine is 25 KDa in molecular weight. In certain embodiments, the positively charged polymer is polyethylenimine, wherein the polyethylenimine is 40 KDa in molecular weight. In certain other embodiments, the positively charged polymer is a mixture of polyethylenimines of different average molecular weights, e.g., having average molecular weights ranging from 1 KDa to 50 KDa, e.g., 10 KDa to 40 KDa, or, e.g., a mixture of 10 KDa and 25 KDa PEI.

In certain embodiments of the invention, the highly-efficient eukaryotic cell transfection (HECT) system may further comprise a eukaryotic cell. As such, in one particular embodiment, the invention provides a highly-efficient eukaryotic cell transfection (HECT) system that is capable of mediating transfection of purified, unencumbered exogenous nucleic acid into a eukaryotic cell comprising a cell transfection medium pre-conditioned with a positively charged polymer, and a eukaryotic cell (e.g., CHO cell, a HEK293 cell, an insect cell, such as SF9, S2 or a HiFive cell).

In certain embodiments of the highly-efficient eukaryotic cell transfection (HECT) systems of the invention, the transfection of eukaryotic cells is transient transfection.

In certain embodiments of the highly-efficient eukaryotic cell transfection (HECT) systems of the invention, the transfection of eukaryotic cells is stable transfection.

A. Media

A medium suitable for use in systems and methods of the present invention is any medium that is used for the growth of eukaryotic cells, e.g., mammalian primary cells, mammalian cell lines, insect cell lines, fish cell lines, or avian cell lines. In light of the inventions described herein, commercially available media that may be used in the systems and methods of the present invention include, but are not limited to, all versions and varieties of ProCHO™ or PowerCHO™ Advance (Lonza), e.g., ProCHO5™, CDCHO, CD FortiCHO™, CD OptiCHO™ (ThermoFisher Scientific), Freestyle™CHO (ThermoFisher Scientific), Hycell CHO HyClone® (GE Life Sciences), DMEM-Dulbecco's Modified Eagle Medium (ThermoFisher Scientific), RPMI media (ThermoFisher Scientific, Sigma-Aldrich, Gibco, etc.), MEM—Minimum Essential Media (Gibco™), IMDM-Iscove's Modified Dulbecco's Medium (ThermoFisher Scientific), Opti-MEM™ Reduced Serum Media (Gibco™), CHO DHFR—Medium (Sigma Aldrich), EXCEL® hybridoma media (Sigma Aldrich), EXCELL® CHO media (Sigma Aldrich), EXCELL® CHOZN® media (Sigma Aldrich), EXCELL® insect cell media (Sigma Aldrich), and the like.

In certain embodiments of the invention, the medium is ProCHO5™ (Lonza).

In certain embodiments of the invention, the medium is CD-CHO (ThermoFisher Scientific).

In certain embodiments of the invention, the medium is Freestyle™ Medium (ThermoFisher Scientific).

In certain embodiments of the invention, the medium is FlexiCHO®-CDM or variations thereof (ExcellGene SA).

In certain embodiments of the invention, the medium is FlexiHEK®-CDM or variants thereof (ExcellGene SA). In certain embodiments of the invention, the medium is FlexiFly®-S2, FlexiFly®-SF9, FlexiFly®-Hi5 or variations thereof (ExcellGene SA).

In certain embodiments' of the invention, the medium may be made in a laboratory rather than purchased or modified by addition of components to a commercially available medium. In one particular embodiment, a representative selection of components, optional components, and range of amounts to use in the formulation of a medium are provided in Table 1. The person of skill in the art working with a preferred cell type or cell line would know and appreciate the components and amounts most suitable for the cell type or cell line.

TABLE 1

Exemplary media components and range of amounts suitable for use in certain embodiments of the present invention for preparing a medium for growing and transfecting mammalian cells (prior to pre-conditioning).

| Medium component | Concentration range mg/L | |
|---|---|---|
| | Low | High |
| Albumin (bovine, human, etc.) | 0 | 10000 |
| Antifoam | 0 | 20000 |
| AMMONIUM METAVANADATE | 0.0001 | 0.0025 |
| AMMONIUM MOLYBDATE 4H2O | 0.001 | 0.005 |
| Animal Casein peptone | 0 | 15000 |
| Animal Peptone P6838 | 0 | 15000 |
| Animal Primatone ® HS | 0 | 15000 |
| Animal Primatone ® HS/UF | 0 | 15000 |
| Animal Primatone ® P37 | 0 | 15000 |

TABLE 1-continued

Exemplary media components and range of amounts suitable for use in certain embodiments of the present invention for preparing a medium for growing and transfecting mammalian cells (prior to pre-conditioning).

| Medium component | Concentration range mg/L Low | High |
|---|---|---|
| Animal Primatone ® RLT | 0 | 15000 |
| Animal Primatone ® RL | 0 | 15000 |
| CADMIUM CL HEMI PENTAHYDRATE | 0 | 2 |
| CALCIUM CHLORIDE | 5 | 200 |
| CALCIUM D-PANTOTHENATE | 0.1 | 7 |
| CHOLINE CHLORIDE | 1 | 150 |
| COBALT CHLORIDE 6H2O | 0.001 | 0.1 |
| COPPER SULFATE-5H2O | 0.001 | 0.02 |
| CUPRIC/COPPER CHLORIDE-2H2O | 0 | 20 |
| D-ALPHA-TOCOPHEROL (Vit. E) | 0 | 1 |
| D-BIOTIN | 0 | 1 |
| D-GLUCOSE | 500 | 15000 |
| D-MANNITOL | 0 | 100 |
| DL-ALPHA-LIPOIC ACID | 0.02 | 1 |
| DL-ALPHA-TOCOPHEROL ACETATE | 0 | 1 |
| ETHANOLAMINE HYDROCHLORIDE | 2 | 100 |
| Fe gluconate 2 $H_2O$ | 0 | 7 |
| FERRIC AMMONIUM CITRATE | 0 | 100 |
| FERRIC NITRATE-9$H_2O$ | 0 | 0.08 |
| FERROUS SULFATE 7$H_2O$ | 0 | 2 |
| FOLIC ACID | 0 | 100 |
| GALACTOSE | 0 | 5000 |
| GLYCINE | 0 | 500 |
| HEPES, FREE ACID | 3500 | 6600 |
| HYDROCORTISONE | 0.002 | 0.011 |
| HYDROXY-L-PROLINE | 0 | 1000 |
| HYPOXANTHINE in NaOH | 0 | 20 |
| INSULIN-HUMAN RECOMBINANT | 0 | 100 |
| L-A-AMINO-N-BUTYRIC ACID | 0 | 300 |
| L-ALANINE | 0 | 150 |
| L-Alpha-phosphatidylcholin | 0.2 | 1.5 |
| L-ARGININE | 200 | 5000 |
| L-ARGININE-HCL | 200 | 5000 |
| L-ASCORBIC ACID | 0 | 1000 |
| L-ASPARAGINE | 40 | 1000 |
| L-ASPARAGINE-H2O | 40 | 1000 |
| L-ASPARTIC ACID | 20 | 1000 |
| L-CYSTEINE-HCL-H2O | 15 | 150 |
| L-CYSTINE-2HCL | 25 | 250 |
| L-GLUTAMIC ACID | 0 | 1000 |
| L-GLUTAMIC ACID MONOPOTASSIUM $H_2O$ | 0 | 2000 |
| L-Glutamine | 250 | 1000 |
| L-GLUTATHIONE REDUCED | 0 | 1000 |
| L-HISTIDINE | 100 | 500 |
| L-HISTIDINE-HCL-H2O | 0 | 500 |
| L-ISOLEUCINE | 50 | 1000 |
| L-LEUCINE | 50 | 1500 |
| L-LYSINE-HCL | 100 | 1500 |
| L-METHIONINE | 50 | 500 |
| L-ORNITHINE HCL | 0 | 100 |
| L-PHENYLALANINE | 25 | 1000 |
| L-PROLINE | 0 | 1000 |
| L-SERINE | 50 | 500 |
| L-TAURINE | 0 | 1000 |
| L-THREONINE | 50 | 1000 |
| L-Tryptophan | 20 | 500 |
| L-TYROSINE | 25 | 800 |
| L-VALINE | 100 | 1000 |
| LINOLEIC ACID | 0.01 | 2 |
| LONG ®$R^3$ IGF-I HUMAN | 0 | 100 |
| MAGNESIUM CHLORIDE | 15 | 70 |
| MAGNESIUM SULFATE | 20 | 100 |
| MANGANESE SULFATE H2O | 0.00005 | 4.5 |
| METHYLATED BETA-CYCLODEXTRIN | 0 | 50 |
| MYO-INOSITOL | 1 | 10000 |
| NICKEL SULFATE-6H2O | 0.000025 | 0.0005 |
| NICONTINAMIDE | 0.5 | 30 |
| OLEIC ACID | 0 | 1000 |
| PARA-AMINOBENZOIC ACID | 0.1 | 20 |
| Plant Hypep ® 1510 | 0 | 15000 |
| Plant Hypep ® 4601 | 0 | 15000 |
| Plant HYPEP ® 4601N | 0 | 15000 |
| Plant Hypep ® 4605 | 0 | 15000 |
| Plant Pea peptone A282 | 0 | 15000 |
| Plant PHOSPHOLIPON ® 90G | 0 | 10000 |
| Plant Potato Peptone ET1LS | 0 | 15000 |
| Plant UltraPep ™ Soy | 0 | 15000 |
| POLOXAMER 188 (Pluronic ®, Lutrol ® F68) | 0 | 1000 |
| POTASSIUM CHLORIDE | 250 | 5000 |
| PUTRESCINE-2HCL | 0.025 | 6 |
| PYRIDOXINE-HCL | 0.5 | 30 |
| RIBOFLAVIN | 0.05 | 5 |
| $SeNa_2O_3$ | 0.002 | 0.07 |
| SERUM (HU, BOVINE, EQUINE, ETC.) in % | 0 | 10 |
| SODIUM CHLORIDE | 4000 | 7500 |
| SODIUM CITRATE 2$H_2O$ | 0 | 1000 |
| SODIUM HYDROGEN CARBONATE | 1000 | 2200 |
| SODIUM METASILICATE-9$H_2O$ | 0.02 | 0.4 |
| SODIUM PHOSPHATE DIBASIC | 30 | 100 |
| SODIUM PHOSPHATE MONOBASIC H20 | 30 | 300 |
| SODIUM PYRUVATE | 0 | 1000 |
| SODIUM SELENITE | 0 | 100 |
| STANNOUS CHLORIDE 2$H_2O$ | 0.000025 | 0.0005 |
| STRONTIUM CHLORIDE HEXAHYDRATE | 0 | 100 |
| SUCCINIC ACID | 0 | 1000 |
| SYNTHETIC CHOLESTEROL | 0 | 30 |
| THIAMINE-HCL | 0.5 | 20 |
| Thymidine in NaOH 1M | 0 | 3 |
| TROPOLONE | 0 | 0.5 |
| TWEEN 80 | 0 | 1000 |
| VITAMIN B12 | 0.05 | 5 |
| YEAST EXTRACT, ULTRAFLTR, DRIED | 0 | 10000 |
| ZINC SULFATE-7$H_2O$ | 0.2 | 2 |

TABLE 2

Exemplary media components and range of amounts suitable for use in certain embodiments of the present invention for preparing a medium for growing and transfecting mammalian cells (prior to pre-conditioning).

| Medium component | Concentration ranges mg/L |
|---|---|
| $CaCl_2$ (anhydrous) | 5-200 |
| $MgCl_2$ (anhydrous) | 15-70 |
| $MgSO_4$ (anhydrous) | 20-110 |
| $Na_2HPO_4$ | 30-100 |
| $NaH_2PO_4$ $H_2O$ | 30-300 |
| $SeNa_2O_3$ | 0.002-0.07 |
| Potassium chloride | 280-5000 |
| L-Asparagine $H_2O$ | 40-1050 |
| L-Aspartic acid | 20-1000 |
| L-Isoleucine | 50-1000 |
| L-Leucine | 50-1200 |
| L-Methionine | 50-500 |
| L-Valine | 100-1000 |
| L-Phenylalanine | 25-1000 |
| L-Tyrosine, 2Na, 2$H_2O$ | 25-430 |
| L-Lysine HCl | 100-1200 |
| L-Threonine | 50-1050 |
| L-Histidine | 100-500 |
| L-Serine | 50-500 |
| L-Tryptophan | 2-500 |
| L-Arginine HCl | 200-5000 |
| L-Cysteine | 25-250 |
| L-Cysteine 2HCl | 15-150 |

TABLE 2-continued

Exemplary media components and range of amounts suitable for use in certain embodiments of the present invention for preparing a medium for growing and transfecting mammalian cells (prior to pre-conditioning).

| Component | mg/liter |
|---|---|
| D-Biotin | 0.003-1 |
| Vitamin B12 | 0.05-5 |
| Riboflavin | 0.05-5 |
| Thiamine HCl | 0.5-20 |
| D-calcium pantothenate | 0.1-7 |
| Pyridoxine HCl | 0.5-30 |
| Folic acid | 0.5-20 |
| Choline chloride | 1-150 |
| Myo-inositol | 10-1000 |
| Ethanolamine HCl | 2-100 |
| Putrescine 2HCl | 0.025-6 |
| DL-α-lipoic acid | 0.03-1 |
| Linoleic acid | 0.01-2 |
| D-Glucose | 500-8000 |
| $CuSO_4\ 5H_2O$ | 0.001-0.02 |
| $ZnSO_4\ 7H_2O$ | 0.4-2 |
| $MnSO_4\ H_2O$ | 0.00007-4.5 |
| NaCl | 5000-7500 |

| Optional Components | mg/liter |
|---|---|
| $Fe(NO_3)_3\ 9H2O$ | 0-0.08 |
| $FeSO_4\ 7H_2O$ | 0-2 |
| L-Proline | 0-1000 |
| L-Glutamic acid | 0-1000 |
| Glycine | 0-500 |
| Sodium pyruvate | 0-1000 |
| Hypoxanthine in NaOH 1M | 0-20 |
| Thymidine in NaOH 1M | 0-3 |
| L-Alanine | 0-150 |
| L-Ornithine | 0-100 |
| L-Taurine | 0-1000 |
| L-α-phosphatidylcholine | 0.9-1.1 |
| Hydrocortisone | 0-0.011 |
| HEPES | 0-6600 |
| Lutrol ® F-68 | 0-1100 |
| Iron gluconate, $2H_2O$ | 0-7 |
| Ferric ammonium citrate | 0-200 |
| $CoCl_2\ 6H_2O$ | 0-0.10 |
| $(NH_4)6Mo_7O_{26}\ 4H_2O$ | 0-0.005 |
| $NiSO_4\ 6H_2O$ | 0-0.0005 |
| $Na_2SiO_3\ 9H_2O$ | 0-0.4 |
| $SnCl_2\ 2H_2O$ | 0-0.0005 |
| $NH_4VO_3$ | 0-0.0025 |
| Nicotinamide (B3) | 0-30 |
| p-aminobenzoic acid | 0-20 |
| L-Glutamine | 0-650 |
| $NaHCO_3$ | 0-2200 |
| Ferric citrate | 0-110 |
| Plant derived hydrolysates | 0-20000 |
| Animal derived hydrolysates | 0-20000 |
| Serum | 0-10% |

In certain embodiments of the highly-efficient eukaryotic cell transfection (HECT) systems of the invention, the medium (prior to pre-conditioning) comprises:
  5-200 mg/L CaCl2 (anhydrous);
  15-70 mg/L MgCl2 (anhydrous);
  0.01-0.08 mg/L Fe(NO3)3 9H2O;
  20-110 mg/L MgSO4 (anhydrous);
  30-100 mg/L Na2HPO4;
  30-300 mg/L NaH2PO4 H2O;
  0.002-0.07 mg/L SeNa2O3;
  280-500 mg/L KCl;
  40-1050 mg/L L-Asparagine H2O;
  20-1000 mg/L L-Aspartic acid;
  50-1000 mg/L L-Isoleucine;
  50-1200 mg/L L-Leucine;
  50-500 mg/L L-Methionine;
  100-1000 mg/L L-Valine;
  25-1000 mg/L L-Phenylalanine;
  25-430 mg/L L-Tyrosine, 2Na, 2H2O;
  100-1200 mg/L L-Lysine HCl;
  50-1050 mg/L L-Threonine;
  100-500 mg/L L-Histidine;
  50-500 mg/L L-Serine;
  2-500 mg/L L-Tryptophan;
  200-5000 mg/L L-Arginine HCl;
  25-250 mg/L L-Cysteine;
  15-150 mg/L L-Cysteine 2HCl;
  0.003-1 mg/L D-Biotin;
  0.05-5 mg/L Vitamin B12;
  0.05-5 mg/L Riboflavin;
  0.5-20 mg/L Thiamine HCl;
  0.1-7 mg/L D-calcium pantothenate;
  0.5-30 mg/L Pyridoxine HCl;
  1-20 mg/L Folic acid;
  1-150 mg/L Choline chloride;
  10-1000 mg/L Myo-inositol;
  2-100 mg/L Ethanolamine NCl; 0.025-6 mg/L Putrescine 2HCl;
  0.03-1 mg/L DL-α-lipoic acid;
  0.01-2 mg/L Linoleic acid;
  500-8000 mg/L D-Glucose;
  0.001-0.02 mg/L CuSO4 5H2O;
  0.05-2 mg/L FeSO4 7H2O;
  0.4-2 mg/L ZnSO4 7H2O;
  0.00007-4.5 mg/L MnSO4 H2O;
  5000-7500 mg/L NaCl;
  0-1000 mg/L L-Proline;
  0-1000 mg/L L-Glutamic acid;
  0-500 mg/L Glycine;
  0-1000 mg/L Sodium pyruvate;
  0-20 mg/L Hypoxanthine in NaOH 1M;
  0-3 mg/L Thymidine in NaOH 1M;
  0-150 mg/L L-Alanine;
  0-100 mg/L L-Ornithine;
  0-1000 mg/L L-Taurine;
  0.9-1.1 mg/L L-α-phosphatidylcholine (optional);
  0.009-0.011 mg/L Hydrocortisone (optional);
  5300-6600 mg/L HEPES (optional);
  900-1100 mg/L Lutrol® F-68 (optional);
  5-7 mg/L Iron gluconate, 2H2O (optional);
  0.04-200 mg/L Ferric ammonium citrate (optional);
  0.001-0.10 mg/L CoCl2 6H2O (optional);
  0.001-0.005 mg/L (NH4)6Mo7O26 4H2O (optional);
  0.000025-0.0005 mg/L NiSO4 6H2O (optional);
  0.02-0.4 mg/L Na2SiO3 9H2O (optional);
  0.000025-0.0005 mg/L SnCl2 2H2O (optional);
  0.0001-0.0025 mg/NH4VO3 (optional);
  0.5-30 mg/L Nicotinamide (B3) (optional);
  0.1-20 mg/L p-aminobenzoic acid (optional);
  500-650 mg/L L-Glutamine (optional);
  2000-2200 mg/L NaHCO3 (optional);
  90-110 mg/L Ferric citrate (optional);
  100-20000 mg/L Plant hydrolysates (optional);
  100-20000 mg/L Animal hydrolysates (optional);
  0.1-10% mg/L Serum (optional); or any combination thereof.

Another embodiment of the invention provides a highly-efficient eukaryotic cell transfection (HECT) systems of the invention comprising e.g., a cell transfection medium, e.g., any of the above-referenced media, or e.g., any media according to Table 2, pre-conditioned with a positively charged polymer (e.g., polyethylenimine (PEI), or polylysine, and the like) prior to the addition of cells and prior to the addition of exogenous nucleic acid.

Another embodiment provides highly-efficient eukaryotic cell transfection (HECT) systems of the invention comprising e.g., a cell transfection medium further capable of supporting and facilitating cell growth, e.g., any of the above-referenced media, or e.g., any media according to Table 1, or e.g., any media according to Table 2, or e.g., any media according to a combination of components according to Table 1 and Table 2, pre-conditioned with a positively charged polymer (e.g., polyethylenimine (PEI), or polylysine, and the like) prior to the addition of cells and prior to the addition of exogenous nucleic acid.

In certain embodiments of the invention, the highly-efficient eukaryotic cell transfection (HECT) system is long-term stable. In certain embodiments, the present invention provides a pre-conditioned transfection media comprising PEI capable of being stored long-term (e.g., 30 days or more, e.g., 60 days or more, e.g., 90 days or more, e.g., 180 days or more, or e.g., 350 days or more) while retaining the capacity to mediate the transfection of purified, unencumbered exogenous nucleic acid into a recipient eukaryotic cell, e.g., a mammalian cell, e.g., a human cell or an animal cell. In certain embodiments, the long-term stable HECT systems are capable of retaining the ability to mediate the transfection of purified, unencumbered exogenous nucleic acid into at least 5% of the recipient eukaryotic cells, e.g., about 10% to about 20% of the recipient cells, e.g., about 20% to about 30% of the recipient cells, e.g., about 30% to about 40% of the recipient cells, e.g., about 40% to about 50% of the recipient cells, e.g., about 50% to about 60% of the recipient cells, e.g., about 60% to about 70% of the recipient cells, e.g., about 70% to about 80% of the recipient cells, e.g., about 80% to about 90% of the recipient cells, e.g., about 90% to about 95% of the recipient cells, or more. In certain embodiments, the HECT system comprises linear 25 KDa PEI. In a particular embodiment, the HECT system comprises ProCHO5™ medium comprising approximately 30 mg/L linear 25 KDa PEI. In a specific embodiment, the HECT system further comprises DMSO. In a particular embodiment, the HECT system comprises CHOM4Tx®medium (ExcellGene).

In certain embodiments of the invention, the highly-efficient eukaryotic cell transfection (HECT) system is low-temperature stable. In certain embodiments, the present invention provides a pre-conditioned transfection media comprising 10 KDa PEI capable of being stored at about 4° C., long-term (e.g., 30 days or more, e.g., 60 days or more, e.g., 90 days or more, e.g., 180 days or more, or e.g., 350 days or more) while retaining the capacity to mediate the transfection of purified, unencumbered exogenous nucleic acid into a recipient eukaryotic cell, e.g., a mammalian cell, e.g., a human cell or an animal cell. In certain embodiments, the low-temperature stable HECT systems are capable of retaining the ability to mediate the transfection of purified, unencumbered exogenous nucleic acid into at least 5% of the recipient eukaryotic cells, e.g., about 10% to about 20% of the recipient cells, e.g., about 20% to about 30% of the recipient cells, e.g., about 30% to about 40% of the recipient cells, e.g., about 40% to about 50% of the recipient cells, e.g., about 50% to about 60% of the recipient cells, e.g., about 60% to about 70% of the recipient cells, e.g., about 70% to about 80% of the recipient cells, e.g., about 80% to about 90% of the recipient cells, e.g., about 90% to about 95% of the recipient cells, or more. In a particular embodiment, the HECT system comprises ProCHO5™ medium comprising approximately 11.6 mg/L linear 10 KDa PEI. In a specific embodiment, the HECT system further comprises DMSO. In a particular embodiment, the HECT system comprises ExcellGene's CHOM4Tx®medium.

In certain embodiments of the invention, the highly-efficient eukaryotic cell transfection (HECT) system is freeze-stable. In certain embodiments, the present invention provides a pre-conditioned transfection medium comprising PEI capable of being stored at about −20° C., long-term (e.g., 30 days or more, e.g., 60 days or more, e.g., 90 days or more, e.g., 180 days or more, or e.g., 350 days or more) while retaining the capacity to mediate the transfection of purified, unencumbered exogenous nucleic acid into a recipient eukaryotic cell, e.g., a mammalian cell, e.g., a human cell or an animal cell. In certain embodiments, the freeze-stable HECT systems are capable of retaining the ability to mediate the transfection of purified, unencumbered exogenous nucleic acid into at least 5% of the recipient eukaryotic cells, e.g., about 10% to about 20% of the recipient cells, e.g., about 20% to about 30% of the recipient cells, e.g., about 30% to about 40% of the recipient cells, e.g., about 40% to about 50% of the recipient cells, e.g., about 50% to about 60% of the recipient cells, e.g., about 60% to about 70% of the recipient cells, e.g., about 70% to about 80% of the recipient cells, e.g., about 80% to about 90% of the recipient cells, e.g., about 90% to about 95% of the recipient cells, or more. In certain embodiments, the HECT system comprises linear 10 KDa PEI. In a particular embodiment, the HECT system comprises ProCHO5™ medium comprising approximately 11.6 mg/L linear 10 KDa PEI. In a specific embodiment, the HECT system further comprises DMSO. In a particular embodiment, the HECT system comprises an ExcellGene developed transfection medium CHOM4Tx®.

In certain embodiments of the invention, the highly-efficient eukaryotic cell transfection (HECT) system is freeze-stable. In certain embodiments, the present invention provides a pre-conditioned transfection medium comprising linear 25 KDa PEI capable of being stored at about −20° C., long-term (e.g., 30 days or more, e.g., 60 days or more, e.g., 90 days or more, e.g., 180 days or more, or e.g., 350 days or more) while retaining the capacity to mediate the transfection of purified, unencumbered exogenous nucleic acid into a recipient eukaryotic cell, e.g., a mammalian cell, e.g., a human cell or an animal cell. In certain embodiments, the present invention provides a pre-conditioned transfection medium comprising linear 10 KDa PEI capable of being stored at about −20° C., long-term (e.g., 30 days or more, e.g., 60 days or more, e.g., 90 days or more, e.g., 180 days or more, or e.g., 350 days or more) while retaining the capacity to mediate the transfection of purified, unencumbered exogenous nucleic acid into a recipient eukaryotic cell, e.g., a mammalian cell, e.g., a human cell or an animal cell. In certain embodiments, the present invention provides a pre-conditioned transfection medium comprising linear 40 KDa PEI capable of being stored at about −20° C., long-term (e.g., 30 days or more, e.g., 60 days or more, e.g., 90 days or more, e.g., 180 days or more, or e.g., 350 days or more) while retaining the capacity to mediate the transfection of purified, unencumbered exogenous nucleic acid into a recipient eukaryotic cell, e.g., a mammalian cell, e.g., a human cell or an animal cell. In certain embodiments, the freeze stable HECT systems are capable of retaining the ability to mediate the transfection of purified, unencumbered exogenous nucleic acid into at least 5% of the recipient eukaryotic cells, e.g., about 10% to about 20% of the recipient cells, e.g., about 20% to about 30% of the recipient cells, e.g., about 30% to about 40% of the recipient cells, e.g., about 40% to about 50% of the recipient cells, e.g., about 50% to about 60% of the recipient cells, e.g., about 60% to about 70% of the recipient cells, e.g., about 70% to about 80% of the recipient cells, e.g., about 80% to about 90% of the recipient cells, e.g., about 90% to about 95% of the recipient cells, or more. In certain embodiments, the HECT system comprises 30 mg/L linear 25 KDa PEI. In a particular embodiment, the HECT system comprises ProCHO5™ medium comprising approximately 30 mg/L linear 25 KDa PEI. In a specific embodiment, the HECT system further comprises DMSO. In certain embodiments, the HECT system comprises an ExcellGene transfection medium CHOM4Tx®-1.

In certain embodiments of the invention, the pre-conditioned transfection media comprising PEI of the long-term-stable, low-temperature stable, and freeze-stable highly-efficient eukaryotic cell transfection (HECT) systems are further capable of supporting and facilitating cell growth.

In certain embodiment of the invention, the pre-conditioned transfection media are designed to transfect insect cells, e.g., SF-9 cells, S2 cells, or Hi-five cells; without intending to be limiting with respect to other insect cells. As such, in certain embodiments, the highly-efficient eukaryotic cell transfection (HECT) systems of the invention designed to transfect insect cells comprise a cell transfection medium, e.g., Fly-M4Tx® (ExcellGene SA), further capable of supporting and facilitating insect cell growth, e.g., any of the above-referenced media, or e.g., any media according to Table 3, e.g., any media according to a combination of components according to Table 1 and Table 2, pre-conditioned with a positively charged polymer (e.g., polyethylenimine (PEI), or polylysine, and the like) prior to the addition of insect cells and prior to the addition of exogenous nucleic acid.

TABLE 3

Exemplary media components and range of amounts suitable for use in certain embodiments of the present invention for preparing a medium for growing and transfecting insect cells (prior to pre-conditioning).

| Components | From (mg/L) | To (mg/L) |
|---|---|---|
| Alpha-Ketoglutaric Acid | 10 | 30 |
| Beta-Alanine | 0 | 300 |
| Calcium chloride dihydrate | 200 | 800 |
| Choline chloride | 20 | 100 |
| Cobalt chloride hexahydrate | 0.05 | 0.1 |
| Cupric chloride dihydrate | 0.05 | 0.2 |
| Cyanocobalamine | 0.1 | 0.24 |
| D-Biotin | 0.05 | 0.16 |
| D-Pantothenic acid (hemicalcium) | 0.002 | 0.008 |
| D(+) Fructose | 0 | 1000 |
| D(+) Glucose | 2500 | 12500 |
| D(+) Sucrose | 0 | 2000 |
| Ferrous sulphate heptahydrate | 0 | 0.55 |
| Folic acid | 0.02 | 0.08 |
| Fumaric acid, free acid | 1 | 4.4 |
| Glycine | 100 | 300 |
| Hydroxy-L-Proline | 250 | 1000 |
| L-Arginine hydrochloride | 200 | 800 |
| L-Asparagine | 500 | 2000 |
| L-Aspartic acid | 500 | 1500 |
| L-Cystine dihydrochloride | 100 | 300 |
| L-Glutamic acid | 500 | 2000 |
| L-Histidine hydrochloride | 150 | 248 |
| L-Isoleucine | 200 | 750 |
| L-Leucine | 100 | 250 |
| L-Lysine hydrochloride | 200 | 700 |
| L-Methionine | 200 | 1000 |
| L-Phenylalanine | 200 | 1000 |
| L-Proline | 100 | 500 |
| L-Serine | 100 | 200 |
| L-Threonine | 100 | 200 |
| L-Tryptophan | 100 | 100 |
| L-Tyrosine disodium salt | 250 | 360 |
| L-Valin | 200 | 500 |
| L(−)-Malic Acid, free acid | 10 | 54 |
| Lipid mixture (L0228 Sigma) (in % of vol) | 0 | 2 |
| Magnesium sulphate anhydrous | 250 | 1000 |
| Maltose | 0 | 1000 |
| Manganese chloride | 0.005 | 0.02 |
| Molybdic acid Ammonium tetrahydrate | 0.01 | 0.04 |
| Myo-Inositol | 0.01 | 0.04 |
| Nicotine amide | 0.05 | 0.16 |
| p-Amino benzoic acid (PABA) | 0.1 | 1 |
| Plant Hypep ® 1510 | 0 | 15000 |
| Plant Hypep ® 4601 | 0 | 15000 |
| Plant HYPEP ® 4601N | 0 | 15000 |
| Plant Hypep ® 4605 | 0 | 15000 |
| Plant Pea peptone A282 | 0 | 15000 |
| Plant PHOSPHOLIPON ® 90G | 0 | 15000 |
| Plant Potato Peptone ET1LS | 0 | 15000 |
| Plant UltrPep™ Soy | 0 | 15000 |
| POLOXAMER 188 (F68, Pluronic ®, Koliphore, Pluronic ®) | 0 | 1000 |
| Potassium chloride | 200 | 1200 |
| Pyridoxine hydrochloride | 0.01 | 0.4 |
| Riboflavin | 0.01 | 0.08 |
| Serum (fetal bovine) (in % of vol) | 0 | 5 |
| Sodium bicarbonate | 100 | 400 |
| Sodium dihydrogen phosphate | 200 | 1000 |
| Soy peptone (A3SC, Organotechnie) | 0 | 10000 |
| Succinic acid | 2.4 | 10 |
| Sucrose | 200 | 1700 |
| Thiamine hydrochloride | 0 | 0.08 |
| Yeast extract ultrafiltered | 0 | 10000 |
| Yeastolate (Difco TC) (BD) | 0 | 8000 |
| Zinc chloride | 0.01 | 0.04 |

B. Positively Charged Polymers

The systems and methods of the present invention utilize a positively charged polymer for cell transfection. The positively charged polymer may be selected from any known positively charged polymer which is suitable for pre-conditioning cell transfection medium sufficient to accommodate the systems and methods of the present invention. In certain embodiments, the positively charged polymer is selected from the group consisting of any polyalkylenimine, dialkylaminoalkyl-dextran, polylysine, dendritic polylysine, hyperbranched polylysine analogues, polyarginine, PDMAEMAs (poly(2-(dimethylamino)ethyl methacrylate), polyamido amines, polyamido amine dendrimers (PAMAM), polyacylhydrazone, chitosan, cationic cellulose, cationic dextrans, spermine, dextran-spermine, spermidine, and similar polycationic substances, and derivatives or combinations thereof. Moreover, the amount of positively charged polymer suitable for use in the HECT systems and methods of the present invention is any amount of polymer sufficient to pre-condition the media that results in the transfection of purified, unencumbered exogenous nucleic acid into eukaryotic cells.

In certain embodiments of the present invention, the positively charged polymer is selected from the group consisting of polyalkylenimine, dialkylaminoalkyl-dextran, polylysine, dendritic polylysine, hyperbranched polylysine analogues and derivatives thereof, any naturally occurring polycations (such as Chitosans, cationic cellulose, cationic dextrans, spermines, dextran-spermine, and derivatives thereof), and any derivatives or combinations thereof.

In certain embodiments of the invention, the positively-charge polymer is polyethylenimine. In certain embodiments, the polyethylenimine is linear, branched or hyperbranched. In particular embodiments, the polyethylenimine is linear. In one embodiment, the positively charged polymer used to pre-condition the medium is added at a final concentration of 1 mg/L medium to 50 mg/L medium.

In certain embodiments of the invention, the polyethylenimine is at least 10 KDa in molecular weight. In certain embodiments, the polyethylenimine is 25 KDa in molecular weight. In certain alternative embodiments, the polyethylenimine is 10 KDa in molecular weight. In certain embodiments the polyethylenimine is a mixture of two or more PEI of different average molecular weights, e.g., a mixture of 10 KDa molecular weight and 25 KDa molecular weight PEI, a mixture of 25 KDa molecular weight and 40 KDa molecular weight PEI, a mixture of 10 KDa molecular weight and 40 KDa molecular weight PEI, or a mixture of 10 KDa molecular weight, 25 KDa molecular weight and 40 KDa molecular weight PEI, In one embodiment, the PEI suitable for use in the practice of the HECT system and method of the present invention is linear. In certain embodiments, the linear PEI is deacylated. In certain embodiment, the linear PEI has an average molecular weight of at least 800 Daltons, e.g., 1 to 5 KDa, e.g., 5 to 10 KDa, e.g., 10 to 15 KDa, e.g., 15 to 20 KDa, e.g., 20 to 25 KDa, e.g., 25 to 30 KDa, e.g., 30 to 40 KDa, e.g., 40 to 50 KDa, or more. In certain embodiments, the linear PEI has an average molecular weight of at least 5 KDa, e.g., 5 to 10 KDa, e.g., 10 to 15 KDa, e.g., 15 to 20 KDa, e.g., 20 to 25 KDa, e.g., 25 to 30 KDa, e.g., 30 to 40 KDa, e.g., 40 to 50 KDa, or more. In certain embodiments, the linear PEI has an average molecular weight of at least 10 KDa, e.g., 10 to 15 KDa, e.g., 15 to 20 KDa, e.g., 20 to 25 KDa, e.g., 25 to 30 KDa, e.g., 30 to 40 KDa, e.g., 40 to 50 KDa, or more. In certain embodiments, the linear PEI has an average molecular weight of at least 20 KDa, e.g., 20 to 25 KDa, e.g., 25 to 30 KDa, e.g., 30 to 40 KDa, e.g., 40 to 50 KDa, e.g., 50 to 100 KDa, or more. In one embodiment, the linear PEI has an average molecular weight of about 10 KDa. In another embodiment, the linear PEI has an average molecular weight of about 25 KDa.

In one embodiment, the PEI is linear 10 KDa PEI added at a final concentration of 1 mg/L medium to 50 mg/L medium. In another embodiment, the linear 10 KDa PEI is added at a final concentration of 2 mg/L medium to 40 mg/L medium. In another embodiment, the linear 10 KDa PEI is added at a final concentration of 3 mg/L medium to 30 mg/L medium. In yet another embodiment, the linear 10 KDa PEI is added at a final concentration of 4 mg/L medium to 20 mg/L medium. In another embodiment, the linear 10 KDa PEI is added at a final concentration of 5 mg/L medium to 10 mg/L medium. In another embodiment, the linear 10 KDa PEI is added at a final concentration of 6 mg/L medium to 10 mg/L medium. In another embodiment, the linear 10 KDa PEI is added at a final concentration of 7 mg/L medium to 10 mg/L medium. In another embodiment, the linear 10 KDa PEI is added at a final concentration of 8 mg/L medium to 10 mg/L medium. In another embodiment, the linear 10 KDa PEI is added at a final concentration of 8 mg/L medium to 9 mg/L medium. In another embodiment, the linear 10 KDa PEI is added at a final concentration of 9 mg/L medium to 10 mg/L medium.

In another embodiment, the PEI is linear 25 KDa PEI added at a final concentration of 1 mg/L medium to 50 mg/L medium. In another embodiment, the linear 25 KDa PEI is added at a final concentration of 2 mg/L medium to 40 mg/L medium. In another embodiment, the linear 25 KDa PEI is added at a final concentration of 3 mg/L medium to 30 mg/L medium. In yet another embodiment, the linear 25 KDa PEI is added at a final concentration of 4 mg/L medium to 20 mg/L medium. In another embodiment, the linear 25 KDa PEI is added at a final concentration of 5 mg/L medium to 10 mg/L medium. In another embodiment, the linear 25 KDa PEI is added at a final concentration of 6 mg/L medium to 10 mg/L medium. In another embodiment, the linear 25 KDa PEI is added at a final concentration of 7 mg/L medium to 10 mg/L medium. In another embodiment, the linear 25 KDa PEI is added at a final concentration of 8 mg/L medium to 10 mg/L medium. In another embodiment, the linear 25 KDa PEI is added at a final concentration of 8 mg/L medium to 9 mg/L medium. In another embodiment, the linear 25 KDa PEI is added at a final concentration of 9 mg/L medium to 10 mg/L medium.

C. Purified, Unencumbered Exogenous Nucleic Acid

In certain embodiments of the highly-efficient eukaryotic cell transfection (HECT) systems and methods of the invention, the purified, unencumbered exogenous nucleic acid is free from one or more of the components selected from the group consisting of proteins, cationic lipids, cationic polymers, liposome forming components, calcium phosphates, calcium chloride, nano-particles, metals, polymeric gene carriers, dendrimers, cyclodextrins, and any combination thereof. In particular embodiments, the purified, unencumbered exogenous nucleic acid is free from all components selected from the group consisting of proteins, cationic lipids, cationic polymers, liposome forming components, calcium phosphates, calcium chloride, nano-particles, metals, polymeric gene carriers, dendrimers, and cyclodextrins. In certain embodiments, the purified, unencumbered exogenous nucleic acids may exist in an essentially solvent-free form, e.g., as a pellet of material, or dissolved in an aqueous solution such as purified water, or TE buffer, e.g., 10 mM Tris 1 mM EDTA buffer, and the like.

In one embodiment, the purified, unencumbered nucleic acid suitable for transfection of eukaryotic cells (e.g., mammalian cells such as human cells or animal cells, insect cells, fish cells, plant cells, fungal cells, and avian cells) is any type or form of natural or synthetic polymers of deoxyribonucleic acid (DNA) or ribonucleic acid (RNA), or biopolymers comprising a mix of both deoxyribonucleotides and ribonucleotides (DNA-RNA hybrids), peptide nucleic acid (PNA), or locked nucleic acid (LNA), and the like. In certain embodiments, DNA biopolymers include, but are not limited to, circular DNA forms, e.g., plasmids, linear DNA, e.g., amplified DNA products, e.g., DNA viral genomes, and the like. In a particular embodiment, the DNA biopolymer transfected into a cell using the HECT system and method of the invention is plasmid DNA. In certain embodiments, RNA biopolymers include, but are not limited to, messenger RNA, e.g., mRNA, transfer RNA, e.g., tRNA, ribosomal RNA, e.g., rRNA, heterologous nuclear RNA, e.g., hn-RNA, small nuclear RNA, e.g., sn-RNA, small nucleolar RNA, any type of RNA capable of interfering with the transcription or translation of a gene, such as small interfering RNA, e.g., siRNA, micro RNA, e.g., miRNA, e.g., long-noncoding RNA, e.g., guide RNA, e.g., CRISPR RNA, e.g., short hairpin RNA, e.g., anti-sense RNA, e.g., enhancer RNA, RNA viral genomes, and the like.

In certain embodiments of the invention, the purified, unencumbered exogenous nucleic acid is selected from the group consisting of DNA, RNA, PNA, LNA, and any combination thereof.

In certain embodiments of the invention, the purified, unencumbered exogenous nucleic acid is DNA. In a particular embodiment, the DNA is circular. In a particular embodiment, the DNA is supercoiled DNA. In an alternative particular embodiment, the DNA is linear. In another particular embodiment the purified, unencumbered exogenous nucleic acid is a mixture of linear and/or circular DNA and/or supercoiled DNA. In yet another embodiment, the purified, unencumbered exogenous nucleic acid further comprises sheared DNA.

In certain embodiments of the invention, the purified, unencumbered exogenous nucleic acid is RNA. In certain embodiments, the RNA is selected from the group consisting of mRNA, rRNA, hn-RNA, mi-RNA, sn-RNA, small nucleolar RNA, long-noncoding RNA, guide RNA, micro RNA, CRISPR RNA, anti-sense RNA, small interfering RNA, short hairpin RNA, enhancer RNA, any RNA capable of interfering with gene expression, and/or any combination thereof.

In certain embodiments of the invention, the exogenous nucleic acid has a nucleotide sequence that is 0% to 100% identical to, or complementary to, a DNA or RNA sequence already existing in the recipient cell, e.g., a eukaryotic cell, e.g., a mammalian cell (e.g., a human cell or an animal cell), an insect cell, a fish cell, a plant cell, a fungal cell, or an avian cell. In one embodiment, the sequence of exogenous nucleic acid is not identical to, e.g., may differ in whole or in part, from a sequence already existing in the recipient cell, for example, the exogenous nucleic acid may be different from a DNA or RNA sequence already existing in the recipient cell, for example, 100% different (0% identical), 99% to 90% different (1% to 10% identical), 89% to 80% different (11% to 20% identical), 79% to 70% different (21% to 30% identical), 69% to 60% different (31% to 40% identical), 59% to 50% different (41% to 50% identical), 49% to 40% different (51% to 60% identical), 39% to 30% different (61% to 70% identical), 29% to 20% different (71% to 80% identical), 19% to 10% different (81% to 90% identical), 9% to 1% different (91% to 99% identical), 0.5% different (99.5% identical), 0.1% different (99.9% identical), or even 0.01% different (99.99% identical).

D. Cells

The eukaryotic cells suitable for use with the HECT systems and methods of the present invention are any eukaryotic cells, e.g., mammalian cells (e.g., human cells), animal cells (e.g., fish cells, metazoan cells, or avian cells), insect cells, plant cells, or fungal cells, capable of being transfected with exogenous nucleic acid.

In certain embodiments of the highly-efficient eukaryotic cell transfection (HECT) systems and methods of the invention, eukaryotic cells are mammalian cells, e.g., cultivated mammalian cells. In certain embodiments, the mammalian cells are selected from the group consisting of primary cells isolated from an animal, e.g., from a mammal, e.g., from a hamster (e.g., Chinese hamster ovary (CHO) cells); from a human (e.g., human embryonic kidney cells, human cervical cancer cells, human prostate cancer cells, human adrenocortical cancer cells, human chronic myelogenous leukemia cells, human prostate cancer cells, human breast cancer cells, human bone cancer cells, human neuroblastoma cells, human acute myeloid leukemia cells, or human glioblastoma cells); from a monkey (e.g. monkey kidney epithelial cells); from a mouse (e.g., mouse embryonic calvarium cells); from a rat (e.g., rat pituitary tumor cells or rat pheochromocytoma cells); and from a dog (e.g., dog kidney epithelial cells). In particular embodiments, the mammalian cell is a CHO cell. In specific embodiments, the CHO cell is selected from the group consisting of a CHO-ori derived cell, CHO K1-derived cell, a CHO S-derived cell, CHO DG44-derived cell, a CHOExpress™ cell, and a CHO DUKX B11-derived cell.

In certain embodiments of the invention, the mammalian cell lines suitable for use in practicing the present invention include, but are not limited to any type or species of human embryonic kidney (HEK293) cells; human cervical cancer cells, e.g., HeLa cells; human prostate cancer cells, e.g., DU145; human adrenocortical cancer cells, e.g., H295R; human chronic myelogenous leukemia cells, e.g., KBM-7 cells; human prostate cancer cells, e.g., LNCaP cells, e.g., PC3 cells; human breast cancer cells, e.g., MCF-7 cells, e.g., MDA-MB-468 cells, e.g., T-47D cells; human bone cancer cells, e.g., SaOS-2 cells; human neuroblastoma cells, e.g., SH-SY5Y; human acute myeloid leukemia cells, e.g., THP-1 cells; human glioblastoma cells, e.g., U87; monkey kidney epithelial cells, e.g., Vero cells; mouse embryonic calvarium cells, e.g., MC3T3 cells; rat pituitary tumor cells, e.g., GH3; rat pheochromocytoma cells, e.g., PC12 cells; dog kidney epithelial cells, e.g., MDCK cells; and the like.

In certain embodiments of the invention, the mammalian cells are primary mammalian cells, such as but not limited to, isolated human lymphocytes, peripheral blood mononuclear cells, tumor-infiltrating T-lymphocytes, and the like.

In certain embodiments of the invention, the HECT systems and methods of the present invention may be practiced utilizing non-mammalian, eukaryotic cell lines. In one embodiment, the non-mammalian, eukaryotic cells lines suitable for use in practicing the present invention include cells or cell lines derived from insects, fish or avian species. In certain embodiments, insect cell lines suitable for use in practicing the present invention include, but are not limited to, all species of cells from *Drosophila melanogaster*, e.g., Schneider 2 cells; *Spodoptera frugiperda*, e.g., Sf9 cells, e.g., Sf21 cells; *Trichoplusia ni*, e.g., High Five cells, and the like. In certain embodiments, fish cell lines suitable for use in practicing the present invention include, but are not limited to, all species of Zebra fish fin fibroblast cells, e.g., AB9 cells. In certain embodiments, avian cell lines suitable for use in practicing the present invention include, but are not limited to, chick embryo fibroblasts (CEF); quail fibroblast cells, e.g., QT-6 cells; duck embryo cells (DE); quail fibrosarcoma cells (QF); goose embryonic epithelial cell line (GEE), chicken fibroblast cell lines, e.g., DF-1; and the like.

In certain embodiments of the highly-efficient eukaryotic cell transfection (HECT) systems of the invention, the eukaryotic cell is in culture, e.g., a suspension culture or in an adherently growing culture.

In certain embodiments of the highly-efficient eukaryotic cell transfection (HECT) systems of the invention, the eukaryotic cell is in a culture different from a suspension culture (e.g., which is not limited to an adherent culture or a culture in a fixed-bed bioreactor), e.g., in a culture that supports the formation of organoids in specialized bioreactors.

In one embodiment, the eukaryotic cell transfection system, method and pre-conditioned media is used to transiently transfect the recipient cells. In another embodiment, the eukaryotic cell transfection system, method and pre-conditioned media is used to stably transfect the recipient cells. In light of the disclosure of the present invention, the skilled artisan would know and appreciate the adaptations necessary to transiently or stably transfect a desired recipient cell.

III. Highly-Efficient Eukaryotic Cell Transfection (HECT) Methods of the Invention The systems of the present invention, which comprise a cell transfection medium pre-conditioned with a positively charged polymer that is capable of mediating transfection of purified, unencumbered exogenous nucleic acid into eukaryotic cells may be utilized in methods of highly-efficient eukaryotic cell transfection (HECT), as described herein.

As such, one embodiment of the present invention provides a highly-efficient eukaryotic cell transfection (HECT) method comprising the steps of obtaining a cell transfection medium pre-conditioned with a positively charged polymer that is capable of mediating transfection of purified, unencumbered exogenous nucleic acid into eukaryotic cells, e.g., in accordance with the media of the present invention described herein;

combining eukaryotic cells with the pre-conditioned cell transfection medium to produce cell-supplemented pre-conditioned cell transfection medium; and combining the cell-supplemented pre-conditioned cell transfection medium with purified, unencumbered exogenous nucleic acid, such that the purified, unencumbered exogenous nucleic acid is transfected into the eukaryotic cells in a highly-efficient manner.

Another embodiment of the present invention provides a highly-efficient eukaryotic cell transfection (HECT) method comprising the steps of obtaining a cell transfection medium pre-conditioned with a positively charged polymer that is capable of mediating transfection of purified, unencumbered exogenous nucleic acid into eukaryotic cells, e.g., in accordance with the media of the present invention described herein;

combining the pre-conditioned cell transfection medium with purified, unencumbered exogenous nucleic acid to produce nucleic acid-supplemented pre-conditioned cell transfection medium; and combining eukaryotic cells with the pre-conditioned cell transfection medium comprising purified, unencumbered exogenous nucleic acid, such that the purified, unencumbered exogenous nucleic acid is transfected into the eukaryotic cells in a highly-efficient manner.

Yet another embodiment of the present invention provides a highly-efficient eukaryotic cell transfection (HECT) method comprising the steps of obtaining purified, unencumbered exogenous nucleic acid housed in a vessel suitable for cell transfection;

obtaining a cell transfection medium pre-conditioned with a positively charged polymer that is capable of mediating transfection of into eukaryotic cells, e.g., in accordance with the media of the present invention described herein; combining the pre-conditioned cell transfection medium with the purified, unencumbered exogenous nucleic acid in the vessel to produce nucleic acid-supplemented pre-conditioned cell transfection medium; and combining eukaryotic cells with the pre-conditioned cell transfection medium comprising purified, unencumbered exogenous nucleic acid, such that the purified, unencumbered exogenous nucleic acid is transfected into the eukaryotic cells in a highly-efficient manner.

In certain embodiments of the methods of the invention, the medium comprises any combination of the components listed in Table 1 (prior to pre-conditioning):

0-10000 mg/L Albumin (bovine, human, plant, etc.);
0-20000 mg/L Antifoam;
0.0001-0.0025 mg/L AMMONIUM METAVANADATE;
0.001-0.005 mg/L AMMONIUM MOLYBDATE $4H_2O$;
0-15000 mg/L Animal Casein peptone;
0-15000 mg/L Animal Peptone P6838;
0-15000 mg/L Animal Primatone® HS;
0-15000 mg/L Animal Primatone® HS/UF;
0-15000 mg/L Animal Primatone® P37;
0-15000 mg/L Animal Primatone® RLT;
0-15000 mg/L Animal Primatone® RL;
0-2 mg/L CADMIUM CL HEMI PENTAHYDRATE;
5-200 mg/L CALCIUM CHLORIDE;
0.1-7 mg/L CALCIUM D-PANTOTHENATE;
1-150 mg/L CHOLINE CHLORIDE;
0.001-0.10 mg/L COBALT CHLORIDE $6H_2O$;
0.001-0.02 mg/L COPPER SULFATE-$5H_2O$;
0-20 mg/L CUPRIC/COPPER CHLORIDE-2 $H_2O$;
0-1 mg/L D-ALPHA-TOCOPHEROL;
0.003-1 mg/L D-BIOTIN;
500-8000 mg/L D-GLUCOSE;
0-2000 mg/L DEXTRAN SULFATE
0-100 mg/L D-MANNITOL;
0.03-1 mg/L DL-ALPHA-LIPOIC ACID;
0-1 mg/L DL-ALPHA-TOCOPHEROL ACETATE;
2-100 mg/L ETHANOLAMINE HYDROCHLORIDE;
0-7 mg/L FE GLUCONATE 2 $H_2O$;
0-110 mg/L FERRIC AMMONIUM CITRATE;
0-0.08 mg/L FERRIC NITRATE-9 $H_2O$;
0-2 mg/L FERROUS SULFATE-$7H_2O$;
0-100 mg/L FOLIC ACID;
0-5000 mg/GALACTOSE;
0-500 mg/L GLYCINE;
2000-8600 mg/L HEPES, FREE ACID;
0.009-0.011 mg/L Hydrocortisone;
0-1000 mg/L HYDROXY-L-PROLINE;
0-20 mg/L Hypoxanthine in NaOH;
0-100 mg/L INSULIN-HUMAN RECOMBINANT;
280-1000 mg/L POTASSIUM-CHLORIDE;
0-3000 mg/L L-A-AMINO-N-BUTYRIC ACID;
0-150 mg/L L-ALANINE;
0.9-1.1 mg/L L-alpha-phosphatidylcholin;
200-5000 mg/L L-ARGININE;
200-5000 mg/L L-ARGININE-HCL;
0-1000 mg/L L-ASCORBIC ACID;
40-1050 mg/L L-ASPARAGINE;
40-1000 mg/L L-ASPARAGINE-$H_2O$;
20-1000 mg/L L-ASPARTIC ACID;
15-150 mg/L L-CYSTEINE-HCL-$H_2O$;
25-250 mg/L L-CYSTINE-2HCL;
0-1000 mg/L L-GLUTAMIC ACID;
0-2000 mg/L L-GLUTAMIC ACID MONOPOTASSIUM $H_2O$;
500-1000 mg/L L-Glutamine;
0-1000 mg/L L-GLUTATHIONE REDUCED;
100-500 mg/L L-HISTIDINE;
0-500 mg/L L-HISTIDINE-HCL-$H_2O$;
50-1000 mg/L L-ISOLEUCINE;
50-1200 mg/L L-LEUCINE;
100-1200 mg/L L-LYSINE-HCL;
50-500 mg/L L-METHIONINE;

0-100 mg/L L-ORNITHINE HCL;
25-1000 mg/L L-PHENYLALANINE;
0-1000 mg/L L-PROLINE;
50-500 mg/L L-SERINE;
0-1000 mg/L L-TAURINE;
50-1000 mg/L L-THREONINE;
2-500 mg/L L-Tryptophan;
25-430 mg/L L-TYROSINE-2NA-$_2$H$_2$O;
100-1000 mg/L L-VALINE;
0.01-2 mg/L LINOLEIC ACID;
0-100 mg/L LONG®R3 IGF-I HUMAN;
0-1100 mg/L Lutrol® (Pluronic®) F68;
15-70 mg/L MAGNESIUM CHLORIDE;
20-110 mg/L MAGNESIUM SULFATE;
0.00007-4.5 mg/L MANGANESE SULFATE H$_2$O;
0-50 mg/L METHYLATED BETA-CYCLODEXTRIN;
1-10000 mg/L MYO-INOSITOL;
0.000025-0.0005 mg/L NICKEL SULFATE-6H$_2$O;
0.5-30 mg/L NICONTINAMIDE;
0-1000 mg/L OLEIC ACID;
0.1-20 mg/L PARA-AMINOBENZOIC ACID;
0-15000 mg/L Plant Hypep® 1510;
0-15000 mg/L Plant Hypep® 4601;
0-15000 mg/L Plant HYPEP® 4601N;
0-15000 mg/L Plant Hypep® 4605;
0-15000 mg/L Plant Pea peptone A282;
0-10000 mg/L Plant PHOSPHOLIPON® 90G;
0-15000 mg/L Plant Potato Peptone ET1LS;
0-15000 mg/L Plant UltrPepT™ Soy;
0-1000 mg/L POLOXAMER 188 (Pluronic®, Lutrol® F68);
0.025-6 mg/L PUTRESCINE-2HCL;
0.5-30 mg/L PYRIDOXINE-HCL;
0.05-5 mg/L RIBOFLAVIN;
0.002-0.07 mg/L SeNa2O3;
0-10% SERUM (HUMAN, BOVINE, EQUINE, ETC.);
5000-7500 mg/L SODIUM CHLORIDE;
0-1000 mg/L SODIUM CITRATE 2H$_2$O;
2000-2200 mg/L SODIUM HYDROGEN CARBONATE;
0.02-0.4 mg/L SODIUM METASILICATE-9H$_2$O;
30-100 mg/L SODIUM PHOSPHATE DIBASIC;
30-300 mg/L SODIUM PHOSPHATE MONOBASIC H$_2$O;
0-1000 mg/L SODIUM PYRUVATE;
0-100 mg/L SODIUM SELENITE;
0.000025-0.0005 mg/L STANNOUS CHLORIDE 2H$_2$O;
0-100 mg/L STRONTIUM CHLORIDE HEXAHYDRATE;
0-1000 mg/L SUCCINIC ACID;
0-20 mg/L SYNTHETIC CHOLESTEROL;
0,5-20 mg/L THIAMINE-HCL;
0-3 mg/L THYMIDINE in NaOH 1 M;
0-0.50 mg/L TROPOLONE;
0-1000 mg/L TWEEN 80;
0.05-5 mg/L VITAMIN B12;
0-10000 mg/L YEAST EXTRACT, ULTRAFLTR, DRIED; or
0.4-2 mg/L ZINC SULFATE-7H$_2$O.

In certain embodiments of the methods of the invention, the medium comprises any of the components listed in Table 2 (prior to pre-conditioning):
5-200 mg/L CaCl$_2$ (anhydrous);
15-70 mg/L MgCl$_2$ (anhydrous);
0.01-0.08 mg/L Fe(NO3)3 9H$_2$O;
20-110 mg/L MgSO4 (anhydrous);
30-100 mg/L Na2HPO4;
30-300 mg/L NaH2PO4 H$_2$O;
0.002-0.07 mg/L SeNa$_2$O$_3$;
280-500 mg/L KCl;
40-1050 mg/L L-Asparagine H$_2$O;
20-1000 mg/L L-Aspartic acid;
50-1000 mg/L L-Isoleucine;
50-1200 mg/L L-Leucine;
50-500 mg/L L-Methionine;
100-1000 mg/L L-Valine;
25-1000 mg/L L-Phenylalanine;
25-430 mg/L L-Tyrosine, 2Na, 2H$_2$O;
100-1200 mg/L L-Lysine HCl;
50-1050 mg/L L-Threonine;
100-500 mg/L L-Histidine;
50-500 mg/L L-Serine;
2-500 mg/L L-Tryptophan;
200-5000 mg/L L-Arginine HCl,
25-250 mg/L L-Cysteine;
15-150 mg/L L-Cysteine 2HCl;
0.003-1 mg/L D-Biotin;
0.05-5 mg/L Vitamin B12;
0.05-5 mg/L Riboflavin;
0.5-20 mg/L Thiamine HCl;
0.1-7 mg/L D-calcium pantothenate;
0.5-30 mg/L Pyridoxine HCl;
1-20 mg/L Folic add;
1-150 mg/L Choline chloride;
10-1000 mg/L Myo-inositol;
2-100 mg/L Ethanolamine HCl;
0.025-6 mg/L Putrescine 2HCl;
0.03-1 mg/L DL-α-lipoic add;
0.01-2 mg/L Linoleic add;
500-8000 mg/L D-Glucose;
0.001-0.02 mg/L CuSO4 5H$_2$O;
0.05-2 mg/L FeSO4 7 H$_2$O;
0.4-2 mg/L ZnSO4 7H$_2$O;
0.00007-4.5 mg/L MnSO4 H$_2$O;
5000-7500 mg/L NaCl;
0-1000 mg/L L-Proline;
0-1000 mg/L L-Glutamic add;
0-500 mg/L Glycine;
0-1000 mg/L Sodium pyruvate;
0-20 mg/L Hypoxanthine in NaOH 1M:
0-3 mg/L Thymidine in NaOH 1M;
0-150 mg/L L-Alanine;
0-100 mg/L-Ornithine;
0-1000 mg/L L-Taurine;
0.9-1.1 mg/L L-α-phosphatidylcholine (optional);
0.009-0.011 mg/L Hydrocortisone (optional);
5300-6600 mg/L HEPES (optional);
0-7 mg/L Iron gluconate, 2H$_2$O;
0-200 mg/L Ferric ammonium citrate;
0.001-0.10 mg/L CoCl2 6H$_2$O;
0-0.005 mg/L (NH$_4$)6Mo$_7$O$_{24}$ 4H$_2$O;
0.000025-0.0005 mg/L NiSO$_4$ 6 H$_2$O (optional);
0.02-0.4 mg/L Na$_2$SiO$_3$ 9 H$_2$O (optional);
0.000025-0.0005 mg/L SnCl2 2 H$_2$O (optional);
0.0001-0.0025 mg/L NH$_4$VO$_3$ (optional);
0.5-30 mg/L Nicotinamide (B3) (optional);
0.1-20 mg/L p-aminobenzoic acid (optional);
500-650 mg/L L-Glutamine (optional);
2000-2200 mg/L NaHCO$_3$ (optional);
0-110 mg/L Ferric citrate;
100-20000 mg/L Plant hydrolysates (optional);
100-20000 mg/L Animal hydrolysates (optional); or
0-10% mg/L Serum.

In certain embodiments of the methods of the invention, the medium comprises any of the components listed in Table 3 (prior to pre-conditioning):

| Components | Concentration range | |
|---|---|---|
| | From (mg/L) | To (mg/L) |
| Alpha-Ketoglutaric Acid | 10 | 30 |
| Beta-Alanine | 0 | 300 |
| Calcium chloride dihydrate | 200 | 800 |
| Choline chloride | 20 | 100 |
| Cobalt chloride hexahydrate | 0.05 | 0.1 |
| Cupric chloride dihydrate | 0.05 | 0.2 |
| Cyanocobalamine | 0.1 | 0.24 |
| D-Biotin | 0.05 | 0.16 |
| D-Pantothenic acid (hemicalcium) | 0.002 | 0.008 |
| D(+) Fructose | 0 | 1000 |
| D(+) Glucose | 2500 | 12500 |
| D(+) Sucrose | 0 | 2000 |
| Ferrous sulphate heptahydrate | 0 | 0.55 |
| Folic acid | 0.02 | 0.08 |
| Fumaric acid, free acid | 1 | 4.4 |
| Glycine | 100 | 300 |
| Hydroxy-L-Proline | 250 | 1000 |
| L-Arginine hydrochloride | 200 | 800 |
| L-Asparagine | 500 | 2000 |
| L-Aspartic acid | 500 | 1500 |
| L-Cystine dihydrochloride | 100 | 300 |
| L-Glutamic acid | 500 | 2000 |
| L-Histidine hydrochloride | 150 | 248 |
| L-Isoleucine | 200 | 750 |
| L-Leucine | 100 | 250 |
| L-Lysine hydrochloride | 200 | 700 |
| L-Methionine | 200 | 1000 |
| L-Phenylalanine | 200 | 1000 |
| L-Proline | 100 | 500 |
| L-Serine | 100 | 200 |
| L-Threonine | 100 | 200 |
| L-Tryptophan | 100 | 100 |
| L-Tyrosine disodium salt | 250 | 360 |
| L-Valin | 200 | 500 |
| L(−)-Malic Acid, free acid | 10 | 54 |
| Lipid mixture (L0228 Sigma) (in % of vol) | 0 | 2 |
| Magnesium sulphate anhydrous | 250 | 1000 |
| Maltose | 0 | 1000 |
| Manganese chloride | 0.005 | 0.02 |
| Molybdic acid Ammonium tetrahydrate | 0.01 | 0.04 |
| Myo-Inositol | 0.01 | 0.04 |
| Nicotine amide | 0.05 | 0.16 |
| p-Amino benzoic acid (PABA) | 0.1 | 1 |
| Plant Hypep ® 1510 | 0 | 15000 |
| Plant Hypep ® 4601 | 0 | 15000 |
| Plant HYPEP ® 4601N | 0 | 15000 |
| Plant Hypep ® 4605 | 0 | 15000 |
| Plant Pea peptone A282 | 0 | 15000 |
| Plant PHOSPHOLIPON ® 90G | 0 | 15000 |
| Plant Potato Peptone ET1LS | 0 | 15000 |
| Plant UltrPep ™ Soy | 0 | 15000 |
| POLOXAMER 188 (F68, Pluronic ®, Koliphore, Pluronic ®) | 0 | 1000 |
| Potassium chloride | 200 | 1200 |
| Pyridoxine hydrochloride | 0.01 | 0.4 |
| Riboflavin | 0.01 | 0.08 |
| Serum (fetal bovine) (in % of vol) | 0 | 5 |
| Sodium bicarbonate | 100 | 400 |
| Sodium dihydrogen phosphate | 200 | 1000 |
| Soy peptone (A3SC, Organotechnie) | 0 | 10000 |
| Succinic acid | 2.4 | 10 |
| Sucrose | 200 | 1700 |
| Thiamine hydrochloride | 0 | 0.08 |
| Yeast extract ultrafiltered | 0 | 10000 |
| Yeastolate (Difco TC) (BD) | 0 | 8000 |
| Zinc chloride | 0.01 | 0.04 |

In certain embodiments of the methods of the invention, the positively charged polymer is polyethylenimine. In certain embodiments, the polyethylenimine is linear or branched. In certain embodiments, the polyethylenimine is linear. In particular embodiments, the polyethylenimine is at least 10 KDa in molecular weight. In specific embodiments, the polyethylenimine is 25 KDa in molecular weight. In alternative specific embodiments, the polyethylenimine is 10 KDa in molecular weight. In alternative specific embodiments, the polyethylenimine is 40 KDa in molecular weight. In a specific embodiments, a combination of 10, 25 and 40 KD polythenimines may be used, in any combination of weight ratios to each other (for example such as 1:1:1, 1:2:1, 1:3:1, 3:1:1, etc.), as found to be practical and useful in pre-conditioning media for the purpose of efficiently mediating transfection of cells.

In certain embodiments of the methods of the invention, the eukaryotic cells are transiently transfected.

In certain embodiments of the methods of the invention, the eukaryotic cells are stably transfected.

Figure 8:
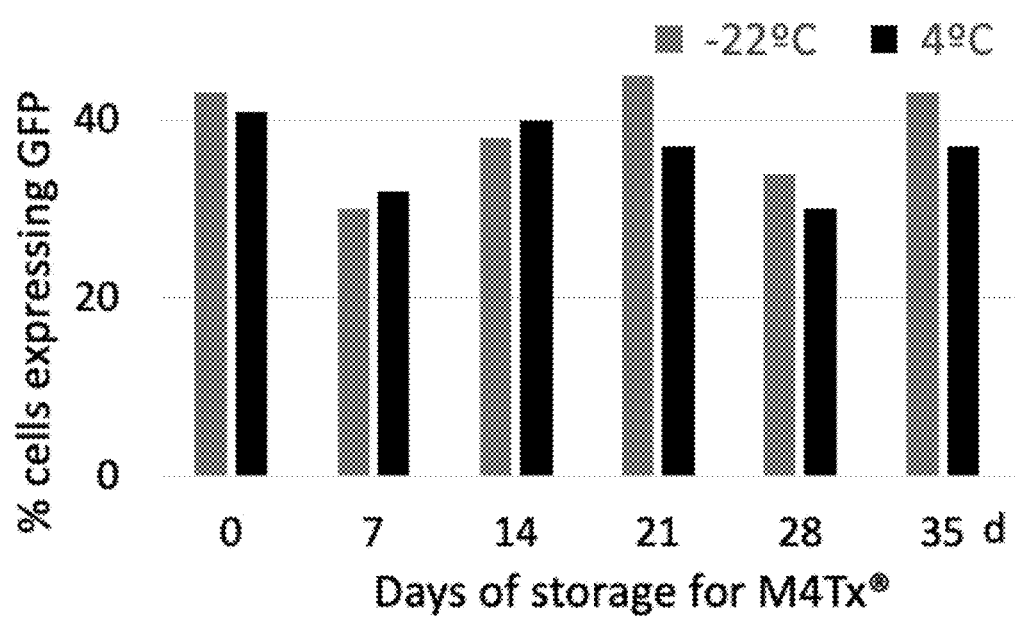
FIG. 8 shows the results of transfections, e.g., the percentage of cells that express the protein GFP after 3 days, of Chinese Hamster Ovary cells (CHOExpress™) with the pEGFP-N1 expression vector using a preconditioned transfection medium (CHOM4Tx®, ExcellGene) that has been stored at −22° C. and 4° C. for up to 35 days.
Figure 9:
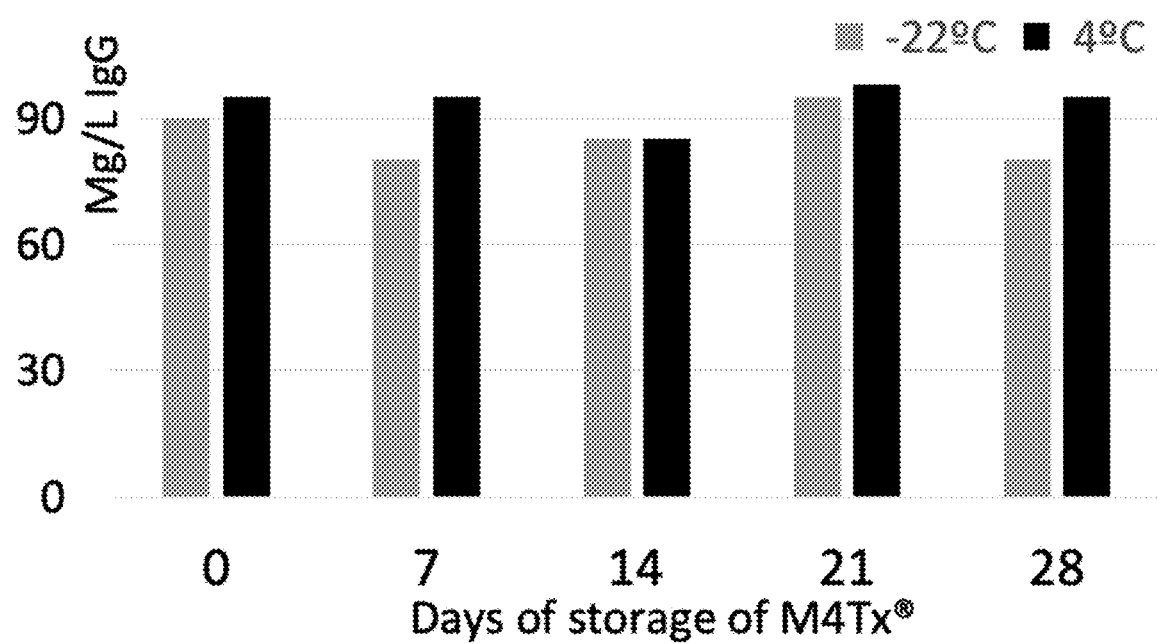
FIG. 9 shows the results of transfections of Chinese Hamster Ovary cells (CHOExpress™), e.g., the product yield after 7 days in mg/L IgG, with the pA3 expression vector using a preconditioned transfection medium (CHOM4Tx®) that has been stored at −22° C. and 4° C. for up to 28 days.

In certain embodiments of the methods of the present invention, the pre-conditioned transfection media are low-temperature-stable, wherein the media are further capable of being held at 4° C. for at least 35 days and retaining the ability to mediate transfection of at least 10% of recipient eukaryotic cells with purified, unencumbered exogenous nucleic acid (FIG. 8), e.g., while also providing expression yields of at least 60 mg/L for an IgG antibody when stored at 4° C. for at least 28 days (FIG. 9).

In certain embodiments of the methods of the present invention, the pre-conditioned transfection media are freeze-stable, wherein the media are further capable of being frozen at −22° C. for at least 35 days and retaining the ability to mediate transfection of at least 10% of recipient eukaryotic cells with purified, unencumbered exogenous nucleic acid (FIG. 8), e.g., while also providing expression yields of at least 60 mg/L for an IgG antibody when stored at −22° C. for at least 28 days (FIG. 9). In certain embodiments, the media comprises polyethylenimine that is 25 KDa in molecular weight. In certain embodiments, the media comprises polyethylenimine that is 10 KDa in molecular weight.

In certain embodiments of the methods of the present invention, the eukaryotic cell is selected from the group consisting of a mammalian cell, a fish cell, an insect cell, and an avian cell. In particular embodiments, the eukaryotic cell is a mammalian cell.

Figure 7:
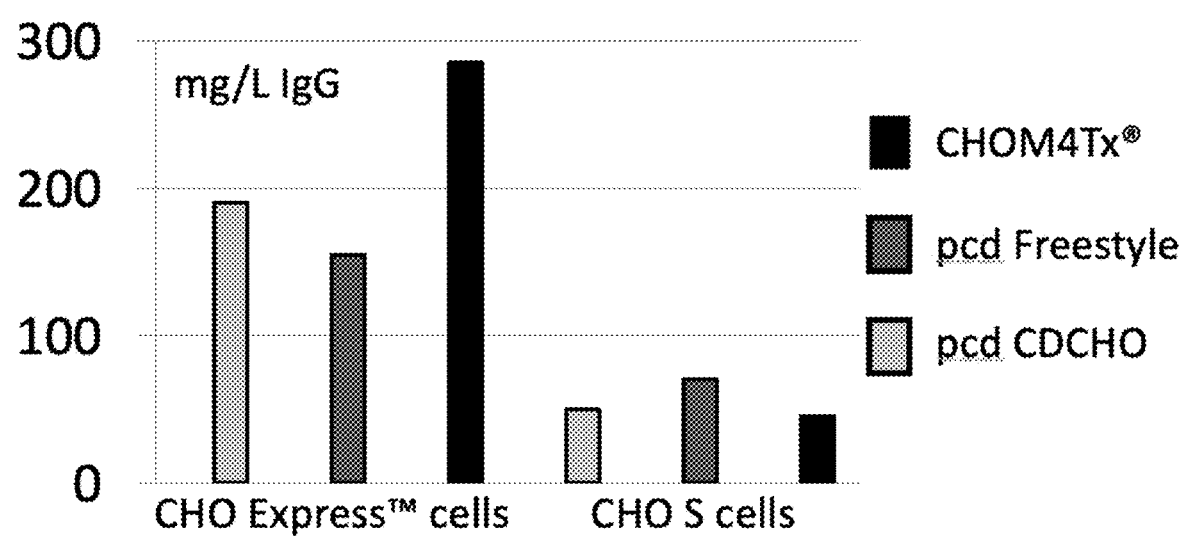
FIG. 7 shows the results of transfections, e.g., the product yield in mg/L of Chinese Hamster Ovary cells (CHOExpress™, CHO S) with the pA3 vector for use in certain embodiments of the present invention using cell culture media from different providers (CHOM4Tx®, ExcellGene, CD-CHO, Freestyle™, ThermoFisher) that were with polymer. CHOExpress™ cells were grown in ProCHO5™ (Lonza) prior to transfection, CHO S cells were grown in CD-CHO medium prior to transfection (pcd: preconditioned).

In certain embodiments of the methods of the present invention, eukaryotic cells are mammalian cells. In certain embodiments, the mammalian cells are selected from the group consisting of primary cells isolated from an animal, from a hamster, e.g., Chinese hamster ovary (CHO) cells, from a human, e.g., human embryonic kidney cells, human cervical cancer cells, human prostate cancer cells, human adrenocortical cancer cells, human chronic myelogenous leukemia cells, human prostate cancer cells, human breast cancer cells, human bone cancer cells, human neuroblastoma cells, human acute myeloid leukemia cells, or human glioblastoma cells, from a monkey, e.g. monkey kidney epithelial cells, from a mouse, e.g., mouse embryonic calvarium cells, from a rat, e.g., rat pituitary tumor cells or rat pheochromocytoma cells, and from a dog, e.g., dog kidney epithelial cells. In particular embodiments, the mammalian cell is a CHO cell. In specific embodiments, the CHO cell is a CHOExpress cell or is a CHO-S cell (FIG. 7). In specific embodiments, the CHO cell is selected from the group consisting of a CHO K1-derived cell, a CHO S-derived cell, CHO DG44-derived cell, a CHOExpress™ cell, and a CHO DUKX B11-derived cell.

Figure 10:
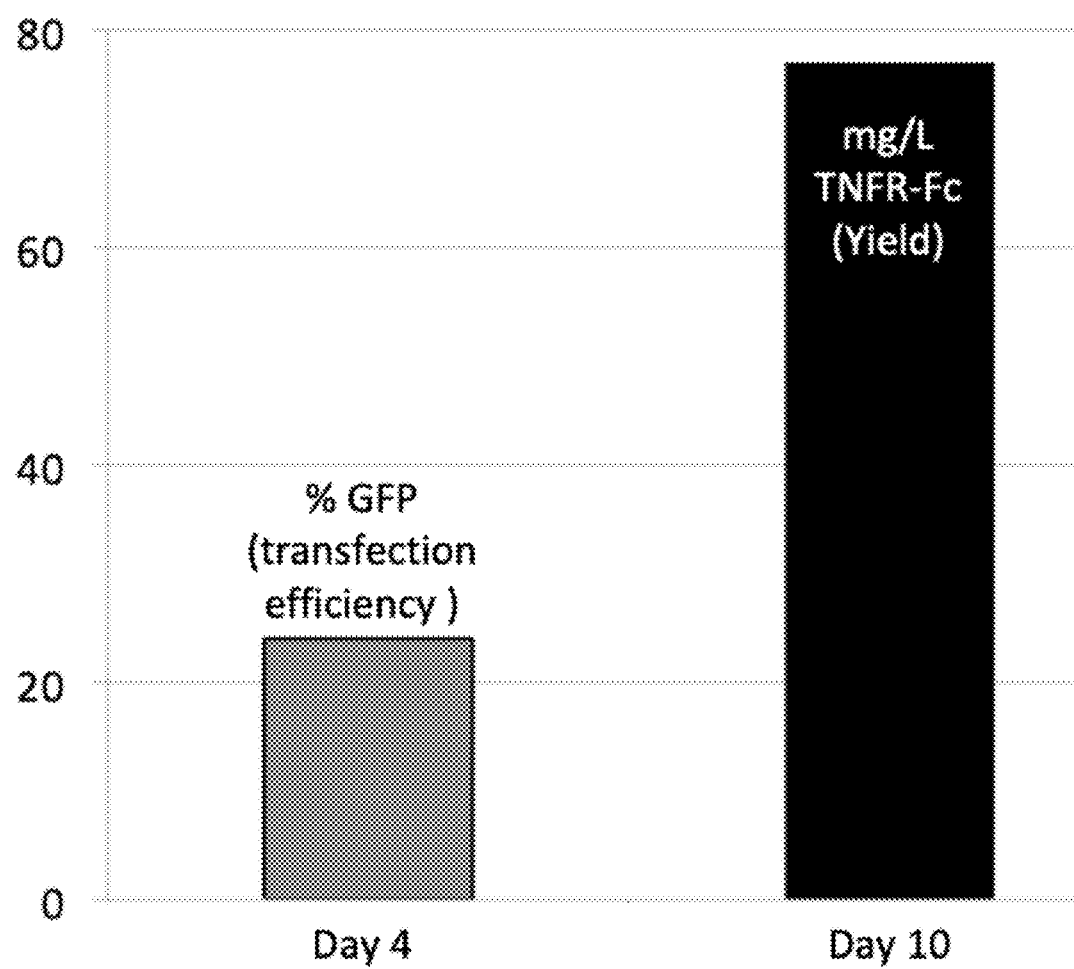
FIG. 10 shows results of a co-transfection of SF-9 cells with a pre-conditioned insect cell medium (Fly-M4Tx®-SF9, ExcellGene) using versions of the pIEX™-10 vectors into which the DNA for E-GFP or TNFR-Fc have been cloned (ratio of vectors in transfections 9:1).
Figure 11:
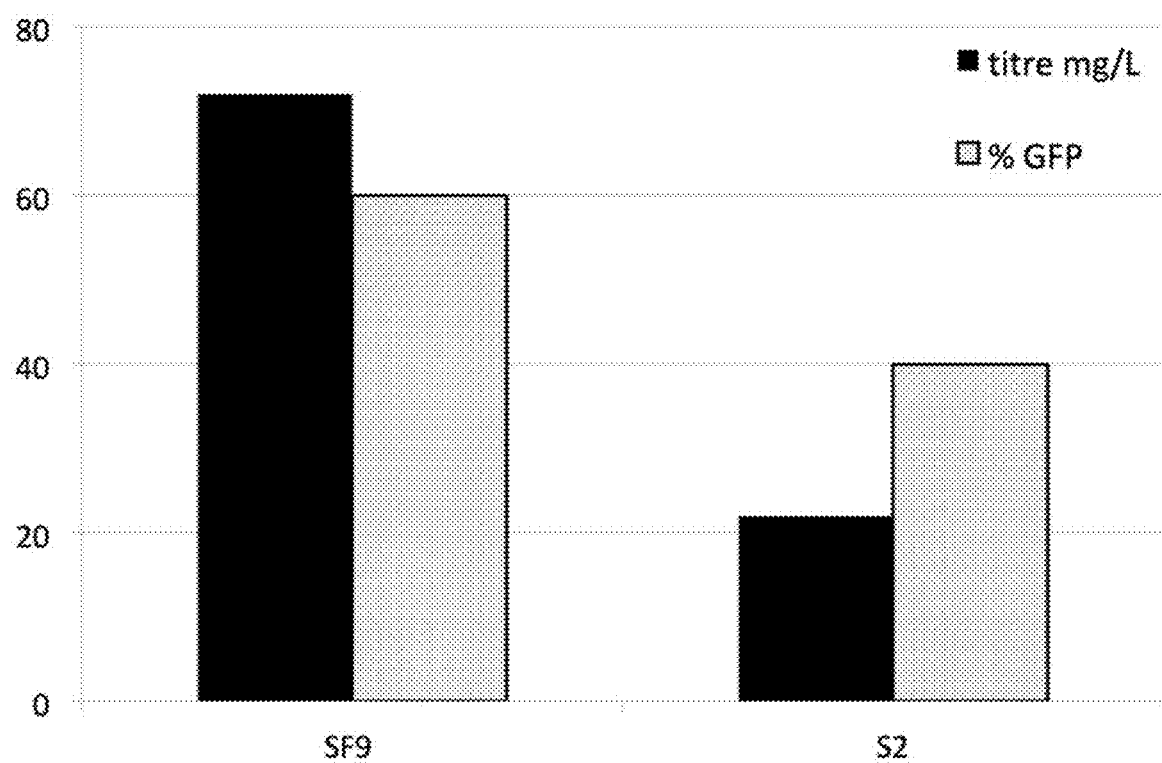
FIG. 11 shows results of co-transfections with SF9 cells and S2 cells with individually pre-conditioned insect cell media (Fly-M4Tx®-SF9, Fly-M4Tx®-S2) using the same pIEX™-10 modified vectors for expression of a TNFR-Fc fusion protein (mg/L) and for expression of GFP (% cells showing fluorescence) (ratio of vectors in transfections 9:1).
Figure 12:
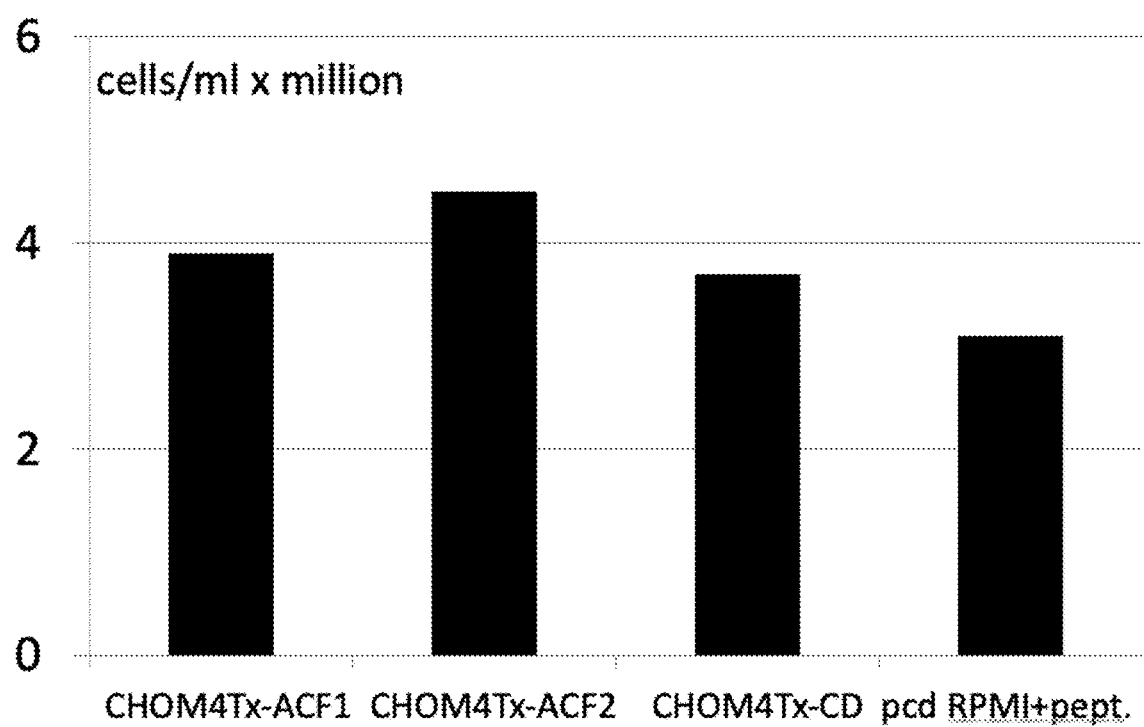
FIG. 12 shows the maximally achieved cell density (day 4) after transfection of CHOExpress™ cells when transfected with different pre-conditioned media (CHOM4Tx®ACF1, CHOM4Tx®ACF2, CHOM4Tx®CD, ExcellGene and preconditioned RPMI medium, to which peptones were added). CD represents the ExcellGene medium FlexiCHO®, a chemically defined medium, ACF1/ACF2 refers to the addition of Soybean peptone (Hypep® 1510, Kerry), added to the transfection media at 2 g/L or 3 g/L. RPMI is the commercially available RPMI1640 (Sigma-Aldrich).The peptone added to the RPMI medium is the same Hypep® 1510, added at 2 g/L.
Figure 13:
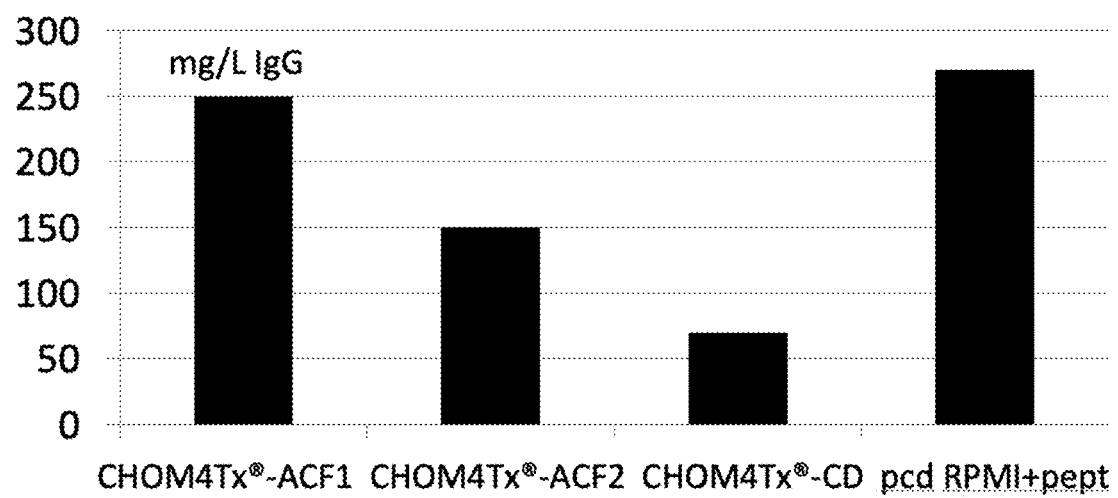
FIG. 13 shows results in terms of IgG yields of transfections into Chinese Hamster Ovary cells (CHOExpress™) that were transfected with different versions of pre-conditioned media, (CHOM4Tx® ACF1, CHOM4Tx® ACF2, CHOM4Tx®CD, pcd RPMI+pept). CD represents the ExcellGene medium FlexiCHO®, a chemically defined medium, ACF1/ACF2 refers to the addition of Soybean peptone (Hypep® 1510, Kerry), added to the transfection media at 2 g/L or 3 g/L. RPMI is the commercially available RPMI1640 (Sigma-Aldrich).
Figure 14:
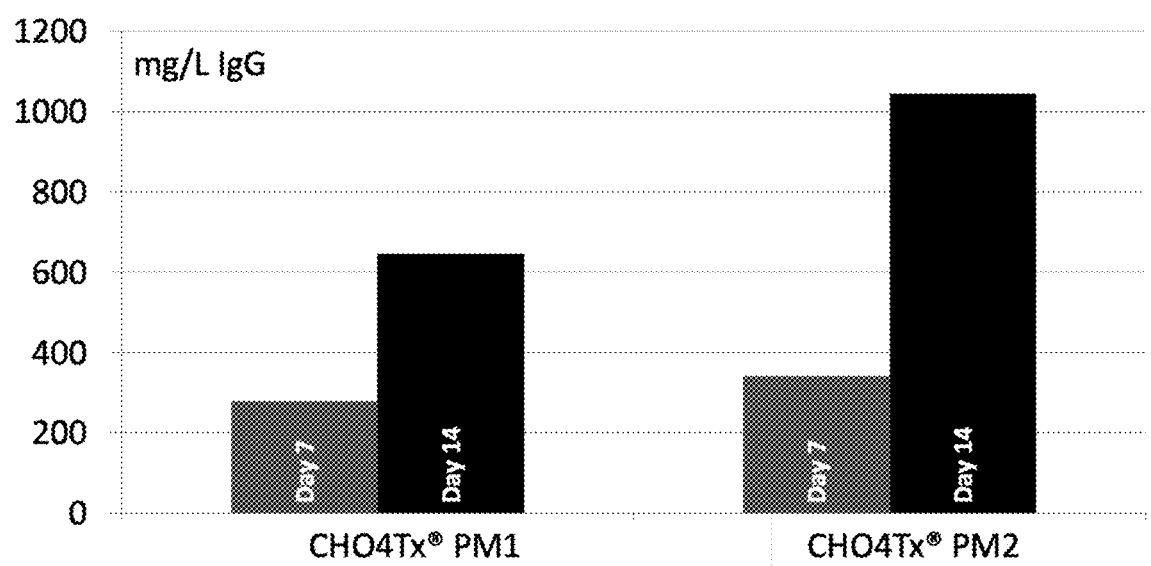
FIG. 14 shows the yield in IgG after 7 or 14 days in the supernatant of CHOExpress™ cells (ExcellGene) when cells were transfected with pre-conditioned CHOM4Tx®medium (ExcellGene) and where a rich, chemically defined composition of concentrated medium was added to the animal-component free medium after transfection (CHOM4Tx® PM1, CHOM4Tx® PM2, ExcellGene)

In certain embodiments of the methods of the present invention, eukaryotic cells are insect cells. In certain embodiments of the methods of the present invention, the insect cells are selected from S2 cells (*Drosophila*), SF9 cells, SF21 cells (*Spodoptera frugiperda*), or HiFive cells (*Trichoplusia ni*). In certain embodiments of the present invention, the selected cells are SF9 cells (FIG. 10 and FIG. 11). In certain embodiments of the present invention, the selected cells are S2 cells (FIG. 11).

In certain embodiments of the methods of the present invention, the purified, unencumbered exogenous nucleic acid is free from one or more of proteins, cationic lipids, cationic polymers, liposome forming components, calcium phosphates, calcium chloride, nano-particles, metals, polymeric gene carriers, dendrimers, and cyclodextrins, or any combination thereof.

In certain embodiments of the methods of the present invention, the purified, unencumbered exogenous nucleic acid is selected from the group consisting of DNA, RNA, PNA, LNA, and any combination thereof.

In certain embodiments of the invention, the purified, unencumbered exogenous nucleic acid is DNA. In a particular embodiment, the DNA is circular. In a particular embodiment, the DNA is supercoiled DNA. In an alternative particular embodiment, the DNA is linear. In another particular embodiment the purified, unencumbered exogenous nucleic acid is a mixture of linear and/or circular DNA and/or supercoiled DNA. In yet another embodiment, the purified, unencumbered exogenous nucleic acid further comprises sheared DNA.

In certain embodiments of the methods of the present invention, the purified, unencumbered exogenous nucleic acid is RNA. In certain embodiments, the RNA is selected from the group consisting of mRNA, rRNA, hn-RNA, mi-RNA, sn-RNA, small nucleolar RNA, long-noncoding RNA, guide RNA, micro RNA, CRISPR RNA, anti-sense RNA, small interfering RNA, short hairpin RNA, enhancer RNA, any RNA capable of interfering with gene expression, and any combination thereof.

IV. Highly-Efficient Eukaryotic Cell Transfection (HECT) Kits of the Invention

The systems of the present invention may further be packaged as a kit for use in highly-efficient transfection of eukaryotic cells. As such, another embodiment of the present invention provides a kit for highly-efficient transfection of eukaryotic cells comprising a highly-efficient eukaryotic cell transfection (HECT) system of the invention, comprising pre-conditioned transfection medium comprising PEI, e.g., 10 KDa PEI or 25 KDa PEI or 40 KDa PEI;

eukaryotic cells compatible with the pre-conditioned transfection medium of the HECT system, wherein said eukaryotic cells are selected from the group consisting of mammalian cells, insect cells, fish cells and avian cells; and a DNA expression vector compatible with said eukaryotic cells. In certain embodiments, the kit is packaged with instructions for use. In particular embodiments, the instructions are associated with the container or packaging, directing use.

In certain embodiments of the kits of the present invention, eukaryotic cells are mammalian cells. In certain embodiments, the mammalian cells are selected from the group consisting of primary cells isolated from an animal, from a hamster, e.g., Chinese hamster ovary (CHO) cells, from a human, e.g., human embryonic kidney cells, human cervical cancer cells, human prostate cancer cells, human adrenocortical cancer cells, human chronic myelogenous leukemia cells, human prostate cancer cells, human breast cancer cells, human bone cancer cells, human neuroblastoma cells, human acute myeloid leukemia cells, or human glioblastoma cells, from a monkey, e.g. monkey kidney epithelial cells, from a mouse, e.g., mouse embryonic calvarium cells, from a rat, e.g., rat pituitary tumor cells or rat pheochromocytoma cells, and from a dog, e.g., dog kidney epithelial cells. In particular embodiments, the mammalian cell is a CHO cell. In specific embodiments, the CHO cell is selected from the group consisting of a CHO K1-derived cell, a CHO S-derived cell, CHO DG44-derived cell, a CHOExpress™ cell, and a CHO DUKX B11-derived cell.

EXEMPLIFICATIONS

In certain embodiments, transfection of eukaryotic cells, e.g., mammalian cells, e.g., CHO cell species, utilizing the highly-efficient cell transfection system, method and pre-conditioned media of the present invention may be carried out according to the following procedures. One skilled in the art, in light of the presently disclosed invention, would know that procedures similar to those described herein may be used to achieve transfection of eukaryotic cells (e.g., mammalian cells, e.g., human cells or animal cells, e.g., CHO cell species) using a variety of nucleic acids (e.g., DNA, e.g., plasmid DNA), and utilizing the highly-efficient eukaryotic cell transfection system, method and pre-conditioned media described herein.

Example 1

PEI Pre-Conditioned CHO Cell Transfection Medium

A. CHOM4Tx®: a PEI Pre-Conditioned Cell Transfection Medium

Immediately after preparation, CHOM4Tx®™ was filter-sterilized through a 0.22 µm filter (Millipore #SCGPT05RE) and stored at 4° C. or −20° C. until use. In certain instances, the medium was aliquoted into eight 10 ml and 100 ml volumes prior to storage.

B. CHOM4Tx®-1™ is a PEI Pre-Conditioned Cell Transfection Medium

Immediately after preparation, CHOM4Tx®-1 transfection medium was filter-sterilized through a 0.22 µm filter (Millipore #SCGPT05RE) and stored at 4° C. or −20° C. until use. In certain instances, the medium was aliquoted into eight 10 mL and 100 mL volumes prior to storage.

C. Preparation of PEI Solution 500 ml UHP water was added into an endotoxin-free, sterile 1 Liter bottle. The liquid was stirred with the help of a pre-sterilized magnetic bar. 1000 mg in weight of PEI was added into the liquid (note: the aggregated consistency of PEI made it difficult to exactly weigh 1 g).

A clean pH probe is introduced into the liquid and observed, and the pH values were obtainded during subsequent steps. The timer was started and immediately 3.7% HCl solution was added dropwise to obtain eventually a pH value of 2.6 to 2.7. (note:

the volume of HCl solution should be around 10 ml).

The solution was allowed to stir for 15 minutes, where if it drifted to a higher pH value, more HCl solution was added until a pH value between 2.6 and 2.7 was obtained. Stirring was continued until a time of 45 minutes had elapsed. The pH was adjusted again to the target value as before. When all PEI was fully resolved, the 1 M NaOH solution was added dropwise while stirring, until a pH of 7.0 was obtained (7-8 ml). About 400 ml of UHP water was added, checking pH. When the pH was found to be slightly lower than pH 7.0 after a short while, a small amount of NaOH was added again to adjust to pH 7.0. Finally, a volume of 1000 ml with UHP water was added.

The entire volume was passed through a 0.22 µm filter under a laminar flow hood into a sterile 1 L bottle, preferably using "Steri-Top" 500 ml units, such as provided by Millipore/Merck or equivalent).

Under laminar flow-hood protection, aliquots of the PEI solution were generated at convenient volumes, such as 5 ml, 10 ml or 20 ml or similar.

Example 2

Highly-Efficient Transient Transfection of CHO Cells Using PEI Pre-Conditioned Cell Transfection Media A. Preparation of CHOExpress™, CHO-S, or CHO-K1 Seed Train Cell Cultures Seed train CHOExpress™, CHO-S, or CHO-K1 cells actively growing in ProCHO5™ medium (Lonza, CAT #BE02-041Q) at 37° C., 5% $CO_2$, and 90% humidity with shaking (180 RPM) were used. Cell density was determined and a volume containing approximately $0.5 \times 10^6$ cells/ml was removed, centrifuged for 3-5 minutes at 3000×g, and the pelleted cells resuspended in fresh, pre-warmed (37° C.) ProCHO5™ medium (Lonza, CAT #BE02-041Q). The cells were grown for 3 days at 37° C., 5% $CO_2$, and 90% humidity with shaking (180 RPM), to reach a density of approximately $3.5 \times 10^6$ cells/ml.

B. Preparation of Cells for Transfection

On day three, approximately 24 hours before cell transfection, the density of the seed train cells was determined. A volume of cells containing approximately $2 \times 10^6$ cells/ml was removed, centrifuged, and the pelleted cells were resuspended in fresh, pre-warmed 37° C. ProCHO5™ medium (Lonza, CAT #BE02-041Q). The cells were grown overnight at 37° C., 5% $CO_2$, and 90% humidity with shaking (180 RPM), to reach a density of at least $5 \times 10^6$ cells/ml.

On the day of transfection, a cell count was carried out on the overnight culture. For each transfection, the appropriate volume of cells was removed, centrifuged, and resuspended in 2 ml or 4 ml pre-conditioned CHOM4Tx®™ transfection medium or PEI pre-conditioned CHOM4Tx®-1™ transfection medium. For a 5 ml transfection, the volume of cells removed and centrifuged was that volume of cells which, when resuspended in 2 ml of CHOM4Tx® or CHOM4Tx®-1™ PEI pre-conditioned media, resulted in a concentration of $10 \times 10^6$ cells/ml. For a 10 ml transfection, the volume of cells removed and centrifuged was that volume of cells which, when resuspended in 4 ml of CHOM4Tx® or CHOM4Tx®-1 PEI pre-conditioned media, resulted in a concentration of $10 \times 10^6$ cells/ml.

C. Transfection

Figure 3:
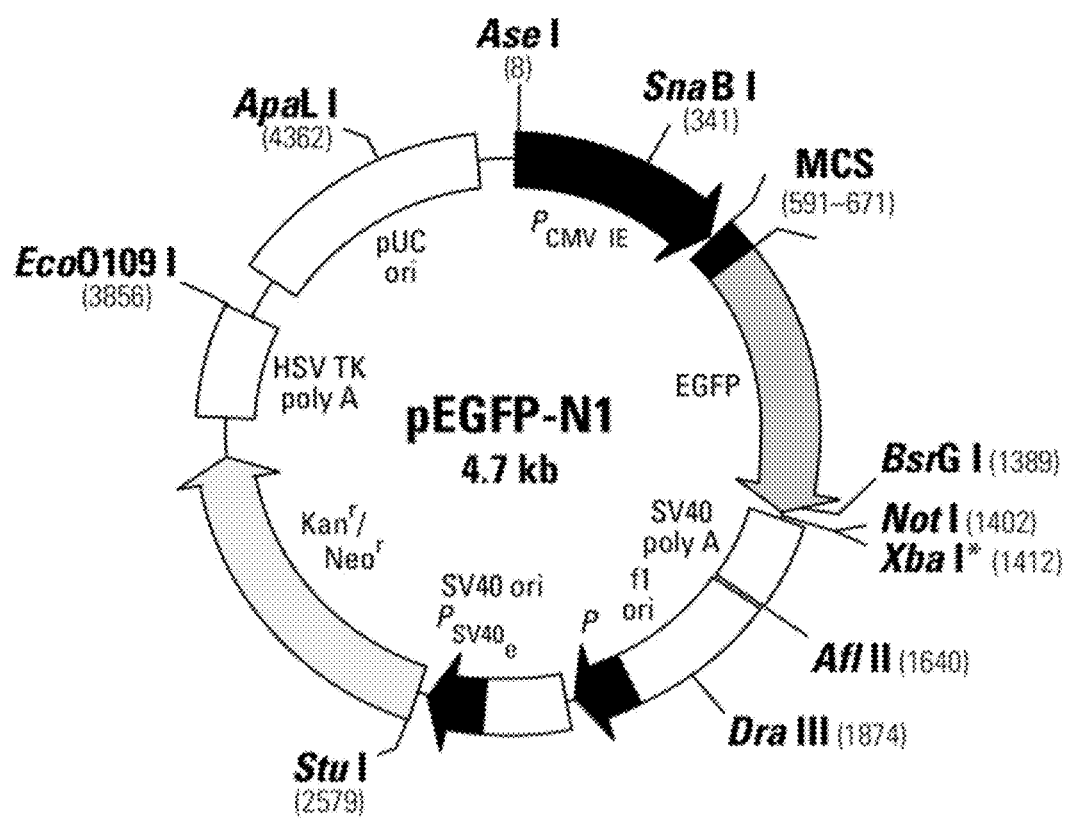
FIG. 3 is a plasmid map of the commercially available pEGFP-N1 (Clonetech) for use in certain embodiments of the present invention. It is capable of supporting the expression of a green fluorescent protein (GFP) in mammalian cells.
Figure 4:
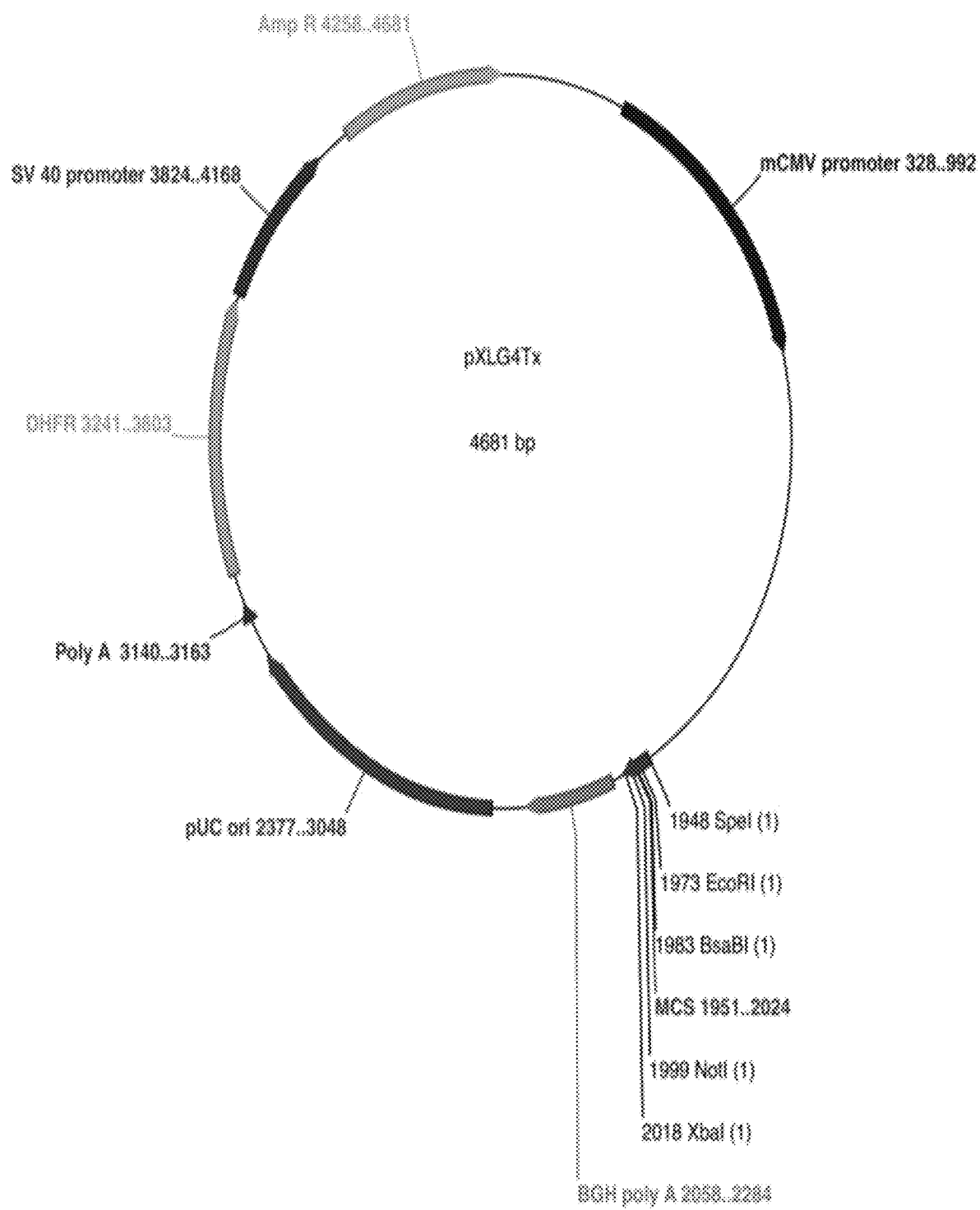
FIG. 4 is a plasmid map of the ExcellGene vector p4Tx® (also referred to as pXLGCHOM4Tx®) for use in certain embodiments of the present invention. Modified versions (i.e., after insertion of desired protein encoding DNA) of this plasmid are capable of supporting the expression of proteins in mammalian cells.

Plasmid DNA expression vector p4Tx® (also named pXLG4Tx®) suitable for transfection and supporting expression in CHOExpress™, CHO-S, or CHO-K1 cells (FIG. 4) containing the gene of interest and thus renamed with the appropriate name, such as p4Tx®-HC and p4Tx®-LC (when an antibody protein was supposed to be expressed) were previously grown in bacteria under standard conditions and purified from the bacterial cells using standard DNA extraction methods well known in the art. In one example, the DNA of interest was encoding an immunoglobulin G (IgG), and two vectors each containing either a heavy chain (HC) construct or a light chain (LC) construct were provided. A third plasmid suitable for expressing in CHOExpress™, CHO-S, or CHO-K1 cells comprising a green fluorescent protein (GFP) reporter gene, pEGFP-N1 (FIG. 3), was also prepared and used for transfection with p4Tx® (FIG. 4). The purified DNA was resuspended in TE buffer to a concentration of 1 µg/µl (comprising a 4.5:4.5:1 ratio of p4Tx®-HC:p4Tx®-LC:pEGFP-N1, respectively by weight) thus generating a solution of purified, unencumbered nucleic acid. The appropriate volume of DNA for each transfection was aliquoted into 50 ml conical tubes.

i. Transfection in CHOM4Tx® Medium:

For a 5 ml transfection, approximately 26 µl of the purified p4Tx® DNA solution, i.e., approximately 26 µg of DNA, was added to the tube. For a 10 ml transfection, approximately 52 µl of the purified DNA solution, i.e., approximately 52 µg of DNA, was added to the tube.

ii. Transfection in CHOM4Tx®-1™ medium: For a 5 ml transfection, approximately 24 µl of the purified p4Tx® DNA solution, i.e., approximately 24 µg of DNA, was added to the tube. For a 10 ml transfection, approximately 48 µl of the purified DNA solution, i.e., approximately 48 µg of DNA, was added to the tube.

The CHOExpress™, CHO-S, or CHO-K1 cells suspended in CHOM4Tx® medium or in CHOM4Tx®-1™ transfection medium were transferred into the DNA-containing tubes and gently mixed. All cells were incubated with shaking (180 RPM) at 31° C., 5% $CO_2$, and 90% humidity for 3 hours.

Following the 3 hour incubation, pre-warmed CHO4Tx® PM(ExcellGene SA) was added to the transfected cells. Three or six ml of the CHO4Tx® PM medium was added to the 5 or 10 ml volumes of transfected cells, respectively.

The CHO4Tx® PM (ExcellGene SA) is an enriched Production medium, optimized for transfections. It is filter-sterilized through a 0.22 µm filter (Millipore #SCGPT05RE) and stored at 4° C. for up to four weeks.

D. Production

The transfected cells were incubated under the conditions described and sampled at various time points to monitor expression of the gene of interest. Typically, the cells were sampled 1 day, 3 days, 7 days, and 14 days after transfection.

E. Controls

Transfection of control CHOExpress™, CHO-S, or CHO-K1 cells was carried out using the conditions described above, utilizing cell culture medium, that was not pre-conditioned with PEI.

F. Results

CHO-K1 cells transfected in CHOM4Tx® media demonstrated excellent cell viability, 84% to 91% viability, and maximal growth in a range from $5.3-7.0 \times 10^6$ cells/ml with approximately 7% to 16% of the cells expressing the GFP reporter gene. On day 7, IgG expression from the transfected cells ranged from approximately 29 to 50 mg/L protein. On day 14, IgG expression from the transfected cells ranged from approximately 37 to 130 mg/L protein (data not shown).

CHO-S cells transfected in CHOM4Tx®-1™ media demonstrated excellent cell viability, 95% to nearly 100% viability, and maximal growth in a range from $4.7-5.6 \times 10^6$ cells/ml, with approximately 10% to 30% of the cells expressing the GFP reporter gene. On day 7, IgG expression from the transfected cells ranged from approximately 30 to 160 mg/L protein. On day 14, IgG expression from the transfected cells ranged from approximately 25 to 290 mg/L protein (data not shown).

Figure 6:
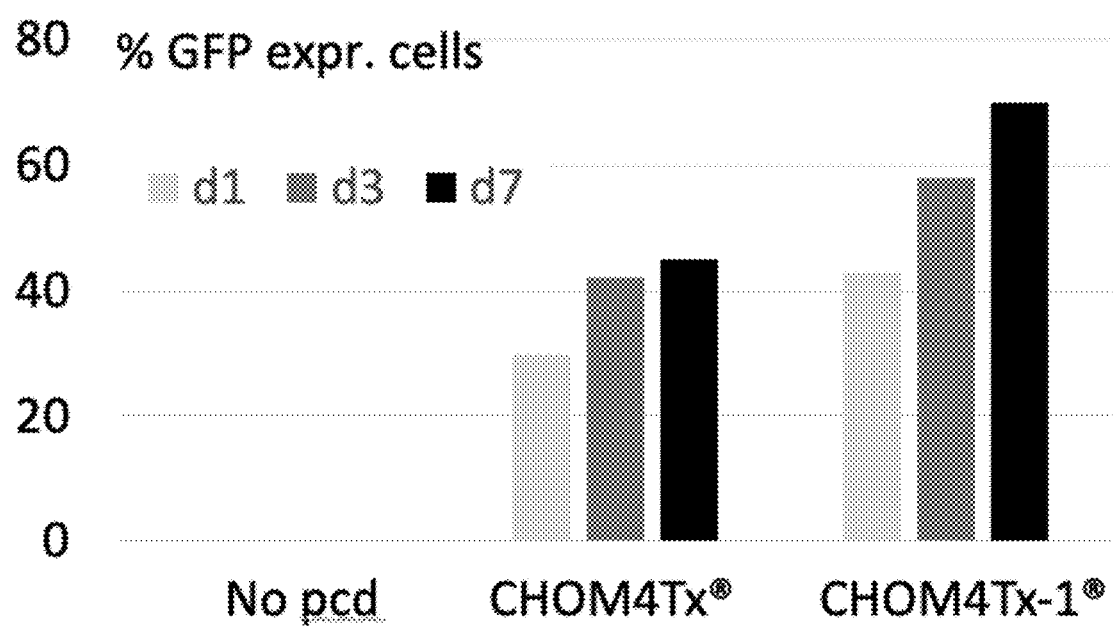
FIG. 6 show the results of transfection of Chinese Hamster Ovary cells (CHOExpress™, ExcellGene) with the pGFP-N1 vector using two versions of cell transfection medium (CHO-M4Tx® and CHO-M4Tx®1®, ExcellGene) in comparison to a control transfection without the pre-conditioning (pcd) for use in certain embodiments of the present invention.

Control transfections carried out in media without PEI (not-preconditioned) resulted in 0 mg/L of IgG protein, and no GFP reporter gene expression was observed (data not shown). For reference of a control transfection without a pre-conditioned medium see FIG. 6.

Similar experiments were conducted with different transfection media such as CD-CHO media or Freestyle™ media pre-conditioned with PEI, for example, 10 KDa PEI, or for example, 25 KDa PEI or for example, 40 KDa, or for example mixtures of two or three of these PEI preparations. Similar to CHOM4Tx® and CHOM4Tx®-1™ media, CDCHO (ThermoFisher Scientific) and Freestyle™ (ThermoFisher Scientific) media pre-conditioned with PEI facilitated the transfection of purified, unencumbered nucleic acid, for example, DNA, into at least 10% of the recipient cells, and resulted in antibody yields of about 50 mg/L in CHO S cells and greater than 150 mg/L in CHOExpress cells (FIG. 7).

Example 3

Highly-Efficient Transient Transfection of CHO Cells Using Stored PEI pre-Conditioned Cell Transfection Medium A. Preparation of Seed Train Cell Cultures Seed train CHOExpress™, CHO-S, or CHO-K1 cells actively growing in ProCHO5™ medium (Lonza, CAT #BE02-041Q) were prepared and used as described. CHOExpress™ cells were also cultured in seed trains in Excell-Gene's chemically defined FlexiCHO® medium.

B. Preparation of Cells for Transfection

CHOExpress™, CHO-S, or CHO-K1 cells collected from the seed train cells were prepared as described. For each transfection, the appropriate volume of cells was removed, centrifuged, and resuspended in 2 ml or 4 ml of previously frozen and thawed CHOM4Tx® medium or CHOM4Tx®-1™ medium.

C. Transfection

Plasmid DNA containing the gene of interest was previously produced in *E.coli* bacteria and purified as described above.

For a 5 ml transfection, approximately 24 µl of the purified DNA solution, i.e., approximately 24 µg of DNA, was added to the tube. For a 10 ml transfection, approximately 48 µl of the purified DNA solution, i.e., approximately 48 µg of DNA, was added to the tube.

The cells suspended in previously frozen and thawed CHOM4Tx® medium or CHOM4Tx®-1 medium were transferred into the DNA-containing tubes and gently mixed. In some samples, dextran sulfate (DS) was added to a final concentration of 1 g/L to the cells and DNA suspended in the medium/cell mixture. The cells were incubated with shaking (180 RPM) at 31° C., 5% $CO_2$, and 90% humidity for 3 hours.

Following the 3 hour incubation, pre-warmed CHO4Tx® PM was added to the transfected cells as described above.

D. Production

The transfected cells were incubated under the conditions described above and sampled at various time points to monitor expression of the gene of interest. Typically, the cells were sampled 1 day, 3 days, 7 days, and 14 days after transfection.

E. Controls

Control transfections in comparison to stored MTx media (4° C., −22° C.) were carried out using the conditions described above, utilizing freshly prepared CHOM4Tx® medium or CHOM4Tx®-1 medium.

F. Results

CHOExpress™ cells transfected in CHOM4Tx® media stored at 4° C. or −22° C. for 0 (control, freshly prepared transfection medium), for 7, 14, 21, 28 or 35 days demonstrated excellent cell viability, approximately 90% to nearly 100% viability, with approximately 30% to 45% of the cells expressing the GFP reporter gene (FIG. 8). In media stored for 0, 7, 14, 21, 28 days at 4° C. or −22° C., IgG expression from the transfected cells sampled at day 7 after transfection was approximately 80 mg/L (80-100 mg/L) protein (FIG. 9). In media stored for about 1 and 7 days at 4° C., IgG expression from the transfected cells sampled at day 14 after transfection was approximately 150 mg/L protein (data not shown graphically).

CHOExpress™ cells transfected in CHOM4Tx® media and stored at 4° C. for 0, 7, 14, 21, 28 or 35 days, where the transfected cells were also supplemented with dextran sulfate, demonstrated excellent cell viability, approximately 90% to nearly 100% viability, with approximately 15% to 45% of the cells expressing the GFP reporter gene (data not shown graphically). In media stored for about 1, 7 and 14 days at 4° C., IgG expression from the transfected cells sampled at day 7 after transfection was approximately 80 mg/L protein. In media stored for about 1 and 7 days at 4° C., IgG expression from the transfected cells sampled at day 14 after transfection ranged from approximately 150 mg/L and 300 mg/L protein, respectively.

CHOExpress™ cells transfected in CHOM4Tx®-1 medium stored at −22° C. for about 0, 7, 14, 21, 28 or 35 days demonstrated excellent cell viability, approximately 95% to nearly 100% viability, with approximately 30% to 45% of the cells expressing the GFP reporter gene. In transfection (pre-conditioned) medium samples stored for about 1, 7 and 14 days at −22° C., IgG expression from the transfected cells sampled at day 7 after transfection was approximately 180 mg/L protein. In medium samples stored for 1 and 7 days at −22° C., IgG expression from the transfected cells sampled at day 14 after transfection was approximately 425 mg/L and 450 mg/L protein, respectively (data not shown graphically).

In other experiments, the CHOM4Tx® and CHOM4Tx®-1 media are stored at 4° C. or −20° C. for longer than 30 days, for example, up to 60 days, or for example, up to 90 days, or longer, and used in transfection experiments. The CHOM4Tx® and CHOM4Tx®-1 media stored at 4° C. or −22° C. up to 60 days, or for up to 90 days, or longer, retain the ability to effect the transfection of purified, exogenous nucleic acid into at least 5%, e.g., at least 10%, of a recipient eukaryotic cell population (data not shown graphically).

Example 4

Highly-Efficient Transient Transfection of Insect Cells Using PEI Pre-Conditioned Cell Transfection Medium At least three different insect cell lines, for example, cell lines derived from *Drosophila melanogaster*, e.g., Schneider 2 (S2) cells, *Spodoptera frugiperda*, e.g., Sf9 cells, e.g., Sf21 cells or *Trichoplusia ni*, e.g., High Five cells, are transfected with purified, unencumbered exogenous nucleic acid, e.g., DNA, utilizing the eukaryotic system, method and pre-conditioned media of the invention. The insect cell culture media are pre-conditioned with about 4 to about 15 g/L PEI, e.g., with 10 KDa PEI or e.g., with 25 KDa PEI or 40 KDa PEI and are called Fly-M4Tx®1, Fly-M4Tx®2, FlyM4Tx®3 (ExcellGene SA).

A. Seed Train Cell Cultures

Seed train cultures of S2, SF9 or Hi-Five cells were maintained at 28° C., in 50 ml OrbShake tubes (10 ml working volume, shaking at 180 rpm in an Incubator Shaker, 50 mm displacement radius) in FlexiFly® medium (S2, SF9, HiFive, respectively) (ExcellGene).

B. Preparation of Cells for Transfection and Transfection

Figure 5:
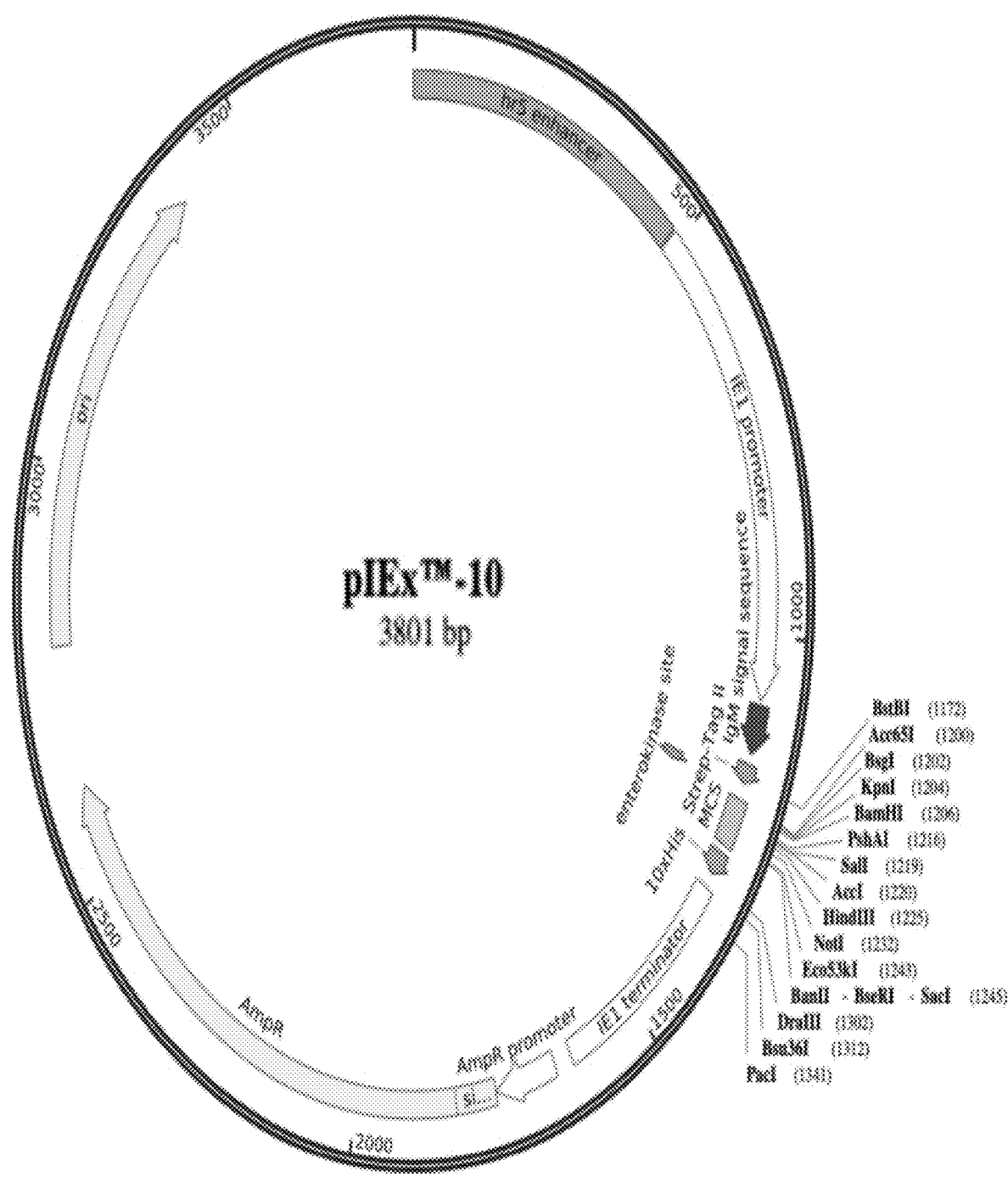
FIG. 5 is a plasmid map of the commercially available pIEX™-10 (Novagen, Darmstadt). Modified versions of this vector, supporting the expression of enhanced green fluorescent protein (E-GFP) or that of a gene for a Tumor Necrosis Factor Receptor—Fc fusion protein (TNFR-Fc), were used in certain embodiments of the present invention, when insect cells were used for expression of protein.

S2, SF9 or Hi-five cells collected from the seed train cultures (day 3) were prepared as follows: On the day of transfection, for each transfection, the appropriate volume of cells was removed, centrifuged, and resuspended into pre-conditioned Fly-MTx®-1 (S2), Fly-M4Tx®-2 (Sf9) or Fly-M4Tx®-3 (HiFive) medium (respectively, depending on the host for transfection) at a density of $2\times10^6$ cells/ml. DNA for transfection, i.e. a mixture of insect cell transfection vectors (FIG. 5) encoding for GFP and for TNFR-Fc was pre-loaded into the 50 ml OrbShake tube prior to transferring the pre-conditioned transfection medium containing the respective cell suspensions of S2 cells and SF-9 cells. Subsequently cells were incubated at 28° C., as described above, for up to 14 days.

The transfection efficiencies were determined on day 4 and the protein yields were determined on day 10.

C Controls

All transfections with PEI-preconditioned Fly-MTx media were controlled by following strictly the protocols for transfections with non-PEI preconditioned media.

D Results

A transfection was executed in a chemically defined, medium for insect cells Fly-M4Tx®-2 (Sf9) (ExcellGene SA). On day 10, a protein yield of 77 mg/L, when executing the post-transfection production phase at 24° C., was observed whereas the transfection efficiency was observed to be 24% on day 4 (FIG. 10).

Equivalent transfections were executed in S2 cells and HiFive cells each done in individually pre-conditioned insect cell media and resulted in similar results as shown in the example (data not shown graphically). Pre-conditioned Fly-M4Tx®-1 (S2) and Fly-M4Tx®-3 (HiFive) (Excell-Gene SA), respectively were used. In all cases, transfection efficiencies>20% (day2-day4) and product yields>30 mg/L were observed.

SF9 and S2 insect cells were transfected with pre-conditioned Fly-M4Tx® media after obtaining seed cultures, as described. Transfection resulted in 40 or 60% efficiency of transfection as measured by GFP staining of cells (day 3) and provided 20 or 70 mg/L of protein (TNFR-Fc) by day 10 (FIG. 11).

Control transfections with non-PEI media resulted in no product synthesis (0 mg/L) and did not show any Green Fluorescent Protein expressing cells.

INCORPORATION BY REFERENCE

The entire contents of all patents, published patent applications and other references cited herein are hereby expressly incorporated herein in their entireties by reference.

Equivalents

Detailed embodiments of the present invention are disclosed here; however, it is to be understood that the disclosed embodiments are merely illustrative of the invention that may be embodied in various forms. In addition, each of the examples given in connection with the various embodiments of the invention is intended to be illustrative, and not restrictive.

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A highly-efficient eukaryotic cell transfection (HECT) system that is capable of mediating transfection of purified, unencumbered exogenous nucleic acid into a eukaryotic cell comprising:
    a cell transfection medium pre-conditioned with a positively charged polymer that is not associated with nucleic acid;
    a eukaryotic cell for combination with said cell transfection medium to produce cell-supplemented pre-conditioned cell transfection medium; and
    a purified, unencumbered exogenous nucleic acid for combination with the cell-supplemented pre-conditioned cell transfection medium, wherein said purified, unencumbered exogenous nucleic acid is free from the components selected from the group consisting of proteins, cationic lipids, cationic polymers, liposome forming components, calcium phosphates, calcium chloride, nano-particles, metals, polymeric gene carriers, dendrimers, and cyclodextrins, for transfection of said purified, unencumbered exogenous nucleic acid into said eukaryotic cell.

2. The highly-efficient eukaryotic cell transfection (HECT) system according to claim 1, wherein said eukaryotic cell is in a suspension culture or in an adherently growing culture.

3. The highly-efficient eukaryotic cell transfection (HECT) system according to claim 1, wherein said cell transfection medium comprises:
    5-200 mg/L $CaCl_2$ (anhydrous);
    15-70 mg/L $MgCl_2$ (anhydrous);
    0-0.08 mg/L $Fe(NO_3)_3$ $9H_2O$;
    20-110 mg/L $MgSO_4$ (anhydrous);
    30-100 mg/L $Na_2HPO_4$;
    30-300 mg/L $NaH_2PO_4$ $H_2O$;
    0.002-0.07 mg/L $SeNa_2O_3$;
    280-500 mg/L KCl;
    40-1050 mg/L L-Asparagine $H_2O$;
    20-1000 mg/L L-Aspartic acid;
    50-1000 mg/L L-Isoleucine;
    50-1200 mg/L L-Leucine;
    50-500 mg/L L-Methionine;
    100-1000 mg/L L-Valine;
    25-1000 mg/L L-Phenylalanine;
    25-430 mg/L L-Tyrosine, 2Na, $2H_2O$;
    100-1200 mg/L L-Lysine HCl;
    50-1050 mg/L L-Threonine;
    100-500 mg/L L-Histidine;
    50-500 mg/L L-Serine;
    2-500 mg/L L-Tryptophan;
    200-5000 mg/L L-Arginine HCl;
    25-250 mg/L L-Cysteine;

15-150 mg/L L-Cysteine 2HCl;
0.003-1 mg/L D-Biotin;
0.05-5 mg/L Vitamin B12;
0.05-5 mg/L Riboflavin;
0.5-20 mg/L Thiamine HCl;
0.1-7 mg/L D-calcium pantothenate;
0.5-30 mg/L Pyridoxine HCl;
1-20 mg/L Folic acid;
1-150 mg/L Choline chloride;
10-1000 mg/L Myo-inositol;
2-100 mg/L Ethanolamine HCl;
0.025-6 mg/L Putrescine 2HCl;
0.03-1 mg/L DL-α-lipoic acid;
0.01-2 mg/L Linoleic acid;
500-8000 mg/L D-Glucose;
0.001-0.02 mg/L $CuSO_4$ $5H_2O$;
0-2 mg/L $FeSO_4$ $7H_2O$;
0.4-2 mg/L $ZnSO_4$ $7H_2O$;
0.00007-4.5 mg/L $MnSO_4$ $H_2O$;
5000-7500 mg/L NaCl;
0-1000 mg/L L-Proline;
0-1000 mg/L L-Glutamic acid;
0-500 mg/L Glycine;
0-1000 mg/L Sodium pyruvate;
0-20 mg/L Hypoxanthine in NaOH 1M;
0-3 mg/L Thymidine in NaOH 1M;
0-150 mg/L L-Alanine;
0-100 mg/L beta-Alanine;
0-100 mg/L L-Ornithine;
0-1000 mg/L L-Taurine;
0.9-1.1 mg/L L-α-phosphatidylcholine;
0.009-0.011 mg/L Hydrocortisone;
5300-6600 mg/L HEPES;
0-1100 mg/L Lutrol® or Pluronic® F-68;
0-7 mg/L Iron gluconate, $2H_2O$;
0-200 mg/L Ferric ammonium citrate;
0.001-0.10 mg/L $CoCl_2$ $6H_2O$;
0.001-0.005 mg/L $(NH_4)_6Mo_7O_{26}$ $4H_2O$;
0.000025-0.0005 mg/L $NiSO_4$ $6H_2O$;
0.02-0.4 mg/L $Na_2SiO_3$ $9H_2O$;
0.000025-0.0005 mg/L $SnCl_2$ $2H_2O$;
0.0001-0.0025 mg/L $NH_4VO_3$;
0.5-30 mg/L Nicotinamide (B3);
0.1-20 mg/L p-aminobenzoic acid;
500-650 mg/L L-Glutamine;
2000-2200 mg/L $NaHCO_3$;
0-110 mg/L Ferric citrate;
0-20000 mg/L Plant hydrolysates;
0-20000 mg/L Animal hydrolysates;
0-10% mg/L Serum, or any combination thereof.

4. The highly-efficient eukaryotic cell transfection (HECT) system comprising according to claim 1, wherein said positively-charge polymer is polyethylenimine.

5. The highly-efficient eukaryotic cell transfection (HECT) system according to claim 4, wherein said polyethylenimine is linear, branched, or hyperbranched.

6. The highly-efficient eukaryotic cell transfection (HECT) system according to claim 5, wherein said polyethylenimine is at least 10 KDa in weight.

7. The highly-efficient eukaryotic cell transfection (HECT) system according to claim 6, wherein said polyethylenimine is 25 KDa in weight.

8. The highly-efficient eukaryotic cell transfection (HECT) system according to claim 1, wherein said eukaryotic cell is selected from the group consisting of a mammalian cell, a fish cell, an insect cell, an avian cell, metazoan cell, and any combination thereof.

9. The highly-efficient eukaryotic cell transfection (HECT) system according to claim 8, wherein said mammalian cell is selected from the group consisting of primary cells isolated from a mammal or are cells that have been established as immortalized cell lines.

10. The highly-efficient eukaryotic cell transfection (HECT) system according to claim 9, wherein said mammalian cell is a CHO cell.

11. The highly-efficient eukaryotic cell transfection (HECT) system according to claim 1, wherein said purified, unencumbered exogenous nucleic acid is selected from the group consisting of DNA, RNA, PNA, LNA, and any combination thereof.

12. A highly-efficient method of transfecting eukaryotic cells comprising
obtaining a cell transfection medium pre-conditioned with a positively charged polymer that is capable of mediating transfection of purified, unencumbered exogenous nucleic acid into eukaryotic cells;
combining eukaryotic cells with said pre-conditioned cell transfection medium to produce cell-supplemented pre-conditioned cell transfection medium; and
combining said cell-supplemented pre-conditioned cell transfection medium with purified, unencumbered exogenous nucleic acid, such that said purified, unencumbered exogenous nucleic acid is transfected into said eukaryotic cells in a highly-efficient manner.

13. The highly-efficient method of transfecting eukaryotic cells according to claim 12, wherein said positively charged polymer is polyethylenimine.

14. The method according to claim 12, wherein said cell transfection medium comprises:
5-200 mg/L $CaCl_2$) (anhydrous);
15-70 mg/L $MgCl_2$ (anhydrous);
0-0.08 mg/L $Fe(NO_3)_3$ $9H_2O$;
20-110 mg/L $MgSO_4$ (anhydrous);
30-100 mg/L $Na_2HPO_4$;
30-300 mg/L $NaH_2PO_4$ $H_2O$;
0.002-0.07 mg/L $SeNa2O_3$;
280-500 mg/L KCl;
40-1050 mg/L L-Asparagine $H_2O$;
20-1000 mg/L L-Aspartic acid;
50-1000 mg/L L-Isoleucine;
50-1200 mg/L L-Leucine;
50-500 mg/L L-Methionine;
100-1000 mg/L L-Valine;
25-1000 mg/L L-Phenylalanine;
25-430 mg/L L-Tyrosine, 2Na, $2H_2O$;
100-1200 mg/L L-Lysine HCl;
50-1050 mg/L L-Threonine;
100-500 mg/L L-Histidine;
50-500 mg/L L-Serine;
2-500 mg/L L-Tryptophan;
200-5000 mg/L L-Arginine HCl;
25-250 mg/L L-Cysteine;
15-150 mg/L L-Cysteine 2HCl;
0.003-1 mg/L D-Biotin;
0.05-5 mg/L Vitamin B12;
0.05-5 mg/L Riboflavin;
0.5-20 mg/L Thiamine HCl;
0.1-7 mg/L D-calcium pantothenate;
0.5-30 mg/L Pyridoxine HCl;
1-20 mg/L Folic acid;
1-150 mg/L Choline chloride;
10-1000 mg/L Myo-inositol;
2-100 mg/L Ethanolamine HCl;
0.025-6 mg/L Putrescine 2HCl;

0.03-1 mg/L DL-α-lipoic acid;
0.01-2 mg/L Linoleic acid;
500-12000 mg/L D-Glucose;
0.001-0.02 mg/L $CuSO_4$ $5H_2O$;
0-2 mg/L $FeSO_4$ $7H_2O$;
0.4-2 mg/L $ZnSO_4$ $7H_2O$;
0.00007-4.5 mg/L $MnSO_4$ $H_2O$;
5000-7500 mg/L NaCl;
0-1000 mg/L L-Proline;
0-1000 mg/L L-Glutamic acid;
0-500 mg/L Glycine;
0-1000 mg/L Sodium pyruvate;
0-20 mg/L Hypoxanthine in NaOH 1M;
0-3 mg/L Thymidine in NaOH 1M;
0-150 mg/L L-Alanine;
0-100 mg/L L-Ornithine;
0-1000 mg/L L-Taurine;
0.9-1.1 mg/L L-α-phosphatidylcholine;
0.009-0.011 mg/L Hydrocortisone;
5300-6600 mg/L HEPES;
900-1100 mg/L Lutrol® F-68;
0-7 mg/L Iron gluconate, $2H_2O$;
0-200 mg/L Ferric ammonium citrate;
0.001-0.10 mg/L $CoCl_2$ $6H_2O$;
0.001-0.005 mg/L $(NH_4)_6Mo_7O_{26}$ $4H_2O$;
0.000025-0.0005 mg/L $NiSO_4$ $6H_2O$;
0.02-0.4 mg/L $Na_2SiO_3$ $9H_2O$;
0.000025-0.0005 mg/L $SnCl_2$ $2H_2O$;
0.0001-0.0025 mg/L $NH_4VO_3$;
0.5-30 mg/L Nicotinamide (B3);
0.1-20 mg/L p-aminobenzoic acid;
500-650 mg/L L-Glutamine;
2000-2200 mg/L $NaHCO_3$;
0-110 mg/L Ferric citrate;
100-20000 mg/L Plant hydrolysates;
100-20000 mg/L Animal hydrolysates;
0.1-10% mg/L Serum, or any combination thereof.

15. The method according to claim 13, wherein said pre-conditioned transfection media is further capable of being held at 4° C. at least 30 days and retaining the ability to mediate transfection of at least 10% of recipient eukaryotic cells with purified, unencumbered exogenous nucleic acid.

16. The method according to claim 13, wherein said pre-conditioned transfection media is further capable of being frozen at least 30 days and retaining the ability to mediate transfection of at least 10% of recipient eukaryotic cells with purified, unencumbered exogenous nucleic acid.

17. A kit for highly efficient transfection of eukaryotic cells comprising the highly efficient eukaryotic cell transfection (HECT) system of claim 7, wherein the eukaryotic cells are compatible with the pre-conditioned boned transfection medium of the HECT system and are selected from the group consisting of mammalian cells, insect cells, fish cells and avian cells; and wherein the purified unencumbered exogenous nucleic acid is a DNA vector compatible with said eukaryotic cells.

18. The kit according to claim 17, wherein said eukaryotic cells are mammalian cells.

* * * * *